United States Patent
Widegren et al.

(10) Patent No.: US 12,421,200 B2
(45) Date of Patent: *Sep. 23, 2025

(54) MANGANESE-CATALYSED HYDROGENATION OF ESTERS

(71) Applicant: University Court of the University of St Andrews, Fife (GB)

(72) Inventors: Magnus Widegren, Fife (GB); Matthew Lee Clarke, Fife (GB)

(73) Assignee: University Court of the University of St Andrews, Fife (GB)

( * ) Notice: Subject to any disclaimer, the term of this patent is extended or adjusted under 35 U.S.C. 154(b) by 872 days.

This patent is subject to a terminal disclaimer.

(21) Appl. No.: 16/960,187

(22) PCT Filed: Jan. 8, 2019

(86) PCT No.: PCT/GB2019/050042
§ 371 (c)(1),
(2) Date: Jul. 6, 2020

(87) PCT Pub. No.: WO2019/138216
PCT Pub. Date: Jul. 18, 2019

(65) Prior Publication Data
US 2021/0053932 A1   Feb. 25, 2021

(30) Foreign Application Priority Data

Jan. 8, 2018 (GB) .................................. 1800276

(51) Int. Cl.
*C07D 307/77* (2006.01)
*B01J 31/18* (2006.01)
*B01J 31/22* (2006.01)

(52) U.S. Cl.
CPC .......... *C07D 307/77* (2013.01); *B01J 31/189* (2013.01); *B01J 31/2295* (2013.01); *B01J 2531/0208* (2013.01); *B01J 2531/72* (2013.01); *B01J 2531/842* (2013.01)

(58) Field of Classification Search
CPC .................................................. C07D 307/77
See application file for complete search history.

(56) References Cited

U.S. PATENT DOCUMENTS

| | | | |
|---|---|---|---|
| 5,274,134 A | 12/1993 | Bruns et al. | |
| 5,463,089 A | 10/1995 | Barton et al. | |
| 2010/0248316 A1 | 9/2010 | Steenkamp et al. | |
| 2016/0318956 A1 | 11/2016 | Quintaine et al. | |
| 2016/0326199 A1* | 11/2016 | Geisser | C07B 41/02 |

FOREIGN PATENT DOCUMENTS

| | | |
|---|---|---|
| EP | 0 165 458 A2 | 12/1985 |
| EP | 0 204 009 A1 | 12/1986 |
| ES | 2 044 780 A1 | 1/1994 |
| ES | 2 195 777 A1 | 12/2003 |
| SU | 988817 A1 | 1/1983 |
| WO | WO 2006/106484 A1 | 10/2006 |
| WO | WO 2013/171302 | 11/2013 |
| WO | WO 2017/068401 A1 | 4/2017 |

OTHER PUBLICATIONS

Widegren, Angewandte Chemie, International Edition (2017), 56(21), 5825-5828.*
Elangovan, Angew. Chem. Int. Ed. 2016, 55, 15364.*
Cooper, Oclue, Chapter 9, 1-21, 2020.*
Cooper, Oclue, Chapter 1, 1-28, 2020.*
Silverstein, Journal of Chemical Education, vol. 94, 2017, pp. 690-695.*
Elangovan, Adv. Synth. Catal.2016, 358, 820-825.*
Dorwald F. A. Side Reactions in Organic Synthesis, 2005, Wiley: VCH, Weinheim p. IX of Preface p. 1-15.*
Widegren ,Organic Letters (2018), 20(9), 2654-2658.*
Widegren Catal. Sci. Technol., 2019, 9, 6047.*
Kallmeier, , Angew. Chem. Int. Ed. 2016, 55, 11806-11809.*
Widegren, Catalysis Science & Technology (2019), 9(21), 6047-6058.*
Younus, Adv. Synth. Catal. 2015, 357, 283-330.*
Elangovan (Angew. Chem. /nt. Ed., 55, 15364-15368 (2016).*
UK IPO Search Report for corresponding GB Application No. GB1800276.6, mailed on Sep. 4, 2018, 18 pages.
CRC Handbook of Chemistry and Physics, 91$^{st}$ Edition, Dissociation Constants of Organic Acids and Bases, and dissociation Constants of Inorganic Acids and Bases, 2010, 12 pages.
Appleton et al., Rhodium (I) Complexes of Ferrocenylphosphines as Efficient Asymmetric Catalysts. The Structure of Fe(n$^5$—C$_5$H$_3$(P(CMe$_3$)$_2$1,3)(n$^5$—C,H$_3$(CHMeNMe$_2$)P(CMe$_3$)$_2$1,2)*, Journal of Organometallic Chemistry, vol. 279, 1985, pp. 5-21.
Blaser et al., "Solvias Josiphos ligands: from discovery to technical applications", Topics in Catalysts, vol. 19, No. 1, Mar. 2002, pp. 3-16.
Cambie et al., "XXX.* Conversion of 8$_x$,13-Epoxylabd-14-Ene into a Compound with an Ambergris-Type Odour", Australian Journal of Chemistry., vol. 24, 1971, pp. 583-591.
Cambie et al., Chemistry of the Podocarpaceae. XXIV.* Some Oxidation Products of (13R)-Labda-8(17), 14-dien-13-ol (Manoo), Australian Journal of Chemistry, vol. 24, 1971, pp. 2365-2377.
Docherty et al., "Activation and discovery of earth-abundant metal catalysts using sodium tert-butoxide", Nature Chemistry, vol. 9, 2017, pp. 595-600.
Elangovan et al., "Hydrogenation of Esters to Alcohols Catalyzed by Defined Manganese Pincer Complexes", Angew. Chem. Int. Ed., vol. 55, 2016, pp. 15364-15368,.

(Continued)

*Primary Examiner* — Nizal S Chandrakumar
(74) *Attorney, Agent, or Firm* — Dority & Manning, P.A.

(57) ABSTRACT

The present invention relates to the field of catalytic hydrogenation and, more particularly, to methods of manganese-catalysed hydrogenation of esters to alcohols. Advantageously, where the esters are chiral, the hydrogenations proceed with high or complete stereochemical integrity.

20 Claims, No Drawings

(56) References Cited

OTHER PUBLICATIONS

Hou et al., "Sterically Hindered Chiral Ferrocdenyl P,N,N-Ligands for Highly Diastereo-/Enantioselective Ir-Catalyzed Hydrogenation of α-Alkyl-ß-ketoesters via Dynamic Kinetic Resolution", Organic Letters, vol. 18, 2016, pp. 5592-5595.
Ito et al., "Catalytic Hydrogenation of Carboxamides and Esters by Well-Defined Cp*Ru Complexes Bearing a Protic Amine Ligand", Journal of the American Chemical Society, vol. 133, 2011, pp. 4240-4242.
Kuriyama et al., "A Homogeneous Catalyst for Reduction of Optically Active Esters to the Corresponding Chiral Alcohols without Loss of Optical Purities", Adv. Synth. Catal., vol. 352, 2010, pp. 92-96.
Kuriyama et al., "Catalytic Hydrogenation of Esters, Development of an Efficient Catalyst and Processes for Synthesising (R)-1,2-Propanediol and 2-(I-Menthoxy)ethanol", Organic Process Research & Development, vol. 16, 2012, pp. 166-171.
Ma et al., "Manganese-Catalyzed Asymmetric Hydrosilylation of Aryl Ketones", ACS Omega, vol. 2, 2017, pp. 4688-4692.
Martinez-Guido et al., "A Multiobjective Optimization Approach for the Development of a Sustainable Supply Chain of a New Fixative in the Perfume Industry", ACS Sustainable Chemistry & Engineering, vol. 2, 2014, pp. 2380-2390.
Moss et al., "Glossary of Class Names of Organic Compounds and Reactive Intermediates Based on Structure", Pure and Appl. Chem., vol. 67, Nos. 8/9, 1955, pp. 1307-1375.
Nguyen et al., "Manganese Pincer Complexes for the Base-Free, Acceptorless Dehydrogenative Coupling of Alcohol to Esters: Development, Scope, and Understanding", ACS Catalysis, vol. 7, 2017, pp. 2022-2032.
Nie et al., "Very Simple and Highly Modular Synthesis of Ferrocene-Based Chiral Phosphines with a Wide Variety of Substituents at the Phosphorus Atom(s)", Organometallics, vol. 33, 2014, pp. 2109-2114.
Nie et al., "Asymmetric hydration of aromatic ketones using an iridium(I) catalyst containing ferrocene-based P—N—N tridentate ligands", Tetrahedron: Asymmetry, vol. 24, 2013, pp. 1567-1571.
Sheldrick, George M., "Crystal structure refinement with SHELXL" Acta Crystallographica Section C, vol. 71, 2015, pp. 3-8.
Silverstein et al., "PK$_a$ Values in the Undergraduate Curriculum: What is the Real pK$_a$ of Water?", Journal of Chemical Education, vol. 94, 2017, pp. 690-695.
Spasyuk et al., "Chemoselective Hydrogenation of Carbonyl Compounds and Acceptorless Dehydrogenative Coupling of Alcohols", Journal of the American Chemical Society, vol. 137, 2015, pp. 3743-3746.
Van Putten et al., "Non-Pincer-Type Manganese Complexes as Efficient Catalysts for the Hydrogenation of Esters", Agnew. Chem. Int. Ed., vol. 56, 2017, pp. 7531-7534.
Vasilenko et al., "Mechanism-Based Enantiodivergence in Manganese Reduction Catalysis: A Chiral Pincer Complex for the Highly Enantioselective Hydroboration of Ketones", Agnew. Chem. Int. Ed., vol. 56, 2017, pp. 8393-8397.
Werkmeister et al., "Catalytic Hydrogenation of Carboxylic Acid Esters, Amides, and Nitriles with Homogeneous Catalysts", Organic Process Research & Development, vol. 18, 2014, pp. 289-302.
Werkmeister et al., "Hydrogenation of Esters to Alcohols with a Well-Defined Iron Complex", Agnew. Chem. Int. Ed., vol. 53, 2014, pp. 8722-8726.
Wu et al., "Iridium Catalysts with f-Amphox Ligands: Asymmetric Hydrogenation of Simple Ketones", Organic Letters, vol. 18, 2016, pp. 2938-2941.
Yang et al., "Iridium-catalyzed asymmetric hydrogenation of racemic x-substituted lactones to chiral diols", Chemical Science, vol. 8, 2017, pp. 1811-1814.
Zhang et al., "Efficient Homogeneous Catalytic Hydrogenation of Esters to Alcohols**", Agnew. Chem. Int. Ed., vol. 118, 2006, pp. 1131-1133.
PCT International Preliminary Report on Patentability for corresponding PCT Application No. PCT/GB2019/050042, mailed on Jul. 23, 2020—10 pages.
PCT International Search Report and Written Opinion for corresponding PCT Application No. PCT/GB2019/050042, mailed on Apr. 3, 2019—12 pages.
Carpenter et al., "Convenient and improved protocols for the hydrogenation of esters using Ru catalysts derived from (P,P), (P,N,N) and (P,N,O) ligands", Dalton Transactions, vol. 41, No. 2012, pp. 10136-101440.
Widegren et al., "Manganese Catalyzed Hydrogenation of Enantiomerically Pure Esters," Organic Letters, vol. 20, No. 9, Apr. 19, 2018, pp. 2654-2658.
Widegren et al., "A Highly Active Manganese Catalyst for Enantioselective Ketone and Ester Hydrogenation" Angew. Chem. Int. Ed., vol. 56, Apr. 20, 2017, pp. 5825-5828.
Kütt, et al., "A Comprehensive Self-Consistent Spectrophotometric Acidity Scale of Neutral Brønsted Acids in Acetonitrile," The Journal of Organic Chemistry, Vo. 71, No. 7, Mar. 9, 2006—50 pages.
Oates et al., "Manganese-catalysed transfer hydrogenation of esters†‡", Chem. Commun., vol. 56, No. 8635, 2020, 4 pages.
Toth et al., "Aspects of the Cleavage of Phosphines with Potassium: Synthesis and Reactivity of Lithium and Potassium Bis(p-(dimethylamino)phenyl)phosphide", Organometallics, vol. 9, 1990, pp. 675-680.
Elangovan et al., Hydrogenation of Esters to Alcohols Catalyzed by Defined Manganese Pincer Complexes, Angewandte Chemie International Edition, vol. 55, 2016, pp. 15364-15368.
Gu et al., "Enantioselective Hydrogenation toward Chiral 3-Aryloxy Tetrahydrofurans Enabled by Spiro Ir-PNN Catalysts Containing an Unusual 5-Substituted Chiral Oxazoline Unit", ACS Catalysis, vol. 12, 2022. pp. 2206-2211.
LibreTexts, "1.20: Dative ligands—CO and phosphines", https://chem.libretexts.org/@go/page/204721, 4 pages.
Ling et al., "Manganese-Catalyzed Enantioselective Hydrogenation of Simple Ketones Using an Imidazole-Based Chiral PNN Tridentate Ligand", Synlett, vol. 31, 2020, pp. 285-289.
Nguyen et al., "Manganese Pincer Complexes for the Base-Free, Acceptorless Dehydrogenative Coupling of Alcohols to Esters: Development, Scope, and Understanding", ACS Catalysis, vol. 7, 2017, pp. 2022-2032.
Reimann et al., "Reactions of Metal Carbonyls. Part 111. t Steric and Stereochemical Limitations of Higher Substitution of Manganese Carbonyl Bromide", Journal of the Chemical Society, Issue 8, 1973, pp. 841-846.
Solvias AG, Ligands and Catalysts Catalogue, "Our chiral and C-X coupling ligands and catalysts", Jan. 2020, 16 pages.
Strem Catalog. "Josiphos", https://www.strem.com/catalog/family/JOSIPHOS/, retrieved on Dec. 14. 2023. 3 pages.
Tondreau et al., "1,2-Addition of Formic or Oxalic Acid to –N{CH2CH2(PiPr2)} 2-Supported Mn(I) Dicarbonyl Complexes and the Manganese-Mediated Decomposition of Formic Acid", Organometallics, vol. 35, 2016, pp. 2049-2052.
Wang et al., "Manganese catalyzed enantio- and regioselective hydrogenation of α,β-unsaturated ketones using an imidazole-based chiral PNN tridentate ligand", Tetrahedron Letters, vol. 82, 2021, 4 pages.
Widegren et al., "A Highly Active Manganese Catalyst for Enantioselective Ketone and Ester Hydrogenation", Angewandte Chemie International Edition, 2017, 85 pages.
Yang et al., "Highly Efficient Asymmetric Hydrogenation Catalyzed by Iridium Complexes with Tridentate Chiral Spiro Aminophosphine Ligands", Accounts of Chemical Research, vol. 56, 2023, pp. 332-349.
Yang et al., "Manganese(I)-catalyzed asymmetric (transfer) hydrogenation of ketones: An insight into the effect of chiral PNN and NN ligands", Journal of Catalysis, vol. 418, 2023, pp. 40-50.
Ziegler et al., "CO, CS, N2, PF3, and CNCH3 as Donors and ir Acceptors. A Theoretical Study by the Hartree-Fock-Slater Transition-State Meth", Inorganic Chemistry, vol. 18, No. 7, 1979, pp. 1755-1759.

(56) References Cited

OTHER PUBLICATIONS

Chinese Office Action (w/ English translation) for corresponding Application No. 201980007452.3, dated Jul. 22, 2024, 18 pages.
Yang et al., "Basic Promotors Impact Thermodynamics and Catalyst Speciation in Homogeneous Carbonyl Hydrogenation", Journal of the American Chemical Society, 2022, 144, 18, pp. 8129-8137.

* cited by examiner

MANGANESE-CATALYSED HYDROGENATION OF ESTERS

CROSS REFERENCE TO RELATED APPLICATIONS

The present application is the national stage entry of International Patent Application No. PCT/GB2019/050042 having a filing date of Jan. 8, 2019, which claims priority to and the benefit of UK Patent Application No. 1800276.6 filed in the UK Patent Office on Jan. 8, 2018, the entire contents of which are incorporated herein by reference.

TECHNICAL FIELD OF THE INVENTION

The present invention relates to the field of catalytic hydrogenation and, more particularly, to methods of manganese-catalysed hydrogenation of esters to alcohols. Advantageously, where the esters are chiral, the hydrogenations proceed with high or complete stereochemical integrity.

STATEMENT REGARDING PRIOR DISCLOSURES BY THE JOINT INVENTORS

M B Widegren, G J Harkness, A M Z Slawin, D B Cordes and M L Clarke (*Angew. Chem. Int. Ed.,* 56, 5825-5828 (2017)) describe the use of a hydrogenation catalyst based on a manganese complex of a chiral P,N,N ligand in the hydrogenation of esters and enantioselective hydrogenation of pro-chiral ketones.

BACKGROUND OF THE INVENTION

The reduction of carbonyl group-containing compounds to alcohols, for example reducing ketones and esters to alcohols, is a fundamental transformation in organic chemistry, and is an integral part of the synthesis of a number of industrial products, including fragrances, pharmaceuticals and fine chemicals. Traditional methods of ester reduction involve reaction of the ester with typically at least two equivalents of a metal or semi-metal hydride. Examples of hydride sources include lithium aluminium hydride, diisobutylaluminium hydride and, in some cases, sodium borohydride. Such reagents are inherently unsafe, have a low atom economy, and a high cost.

Effecting hydrogenation of esters catalytically, using molecular hydrogen, is an attractive alternative, offering potential cost savings and environmental advantages, for example through at least the potential for 100% atom economy. However, although the development of ruthenium catalysts for the reduction of ketones to alcohols, particularly with stereochemical control (for which the Nobel Prize in chemistry was awarded in 2001) is mature technology, catalytically hydrogenating esters is more challenging, owing to the relatively low polarity of the carbonyl group in comparison with that in ketones and aldehydes.

Typical heterogeneous hydrogenation pre-catalysts include Raney nickel, and copper chromite, which require harsh reaction conditions. In contrast, the use of homogeneous catalysis, reviewed by S Werkmeister et al. (*Org. Process Res. Dev.,* 18, 289-302 (2014)) is generally considered to permit use of lower reaction temperatures and hydrogen pressures, giving rise to greater selectivity.

In homogeneously catalysed ester hydrogenations, ruthenium complexes are typically employed as pre-catalysts, stabilised by a variety of ligands. For example ruthenium catalysts have been reported to catalyse the reduction of esters to their corresponding alcohols in patent publications WO 2006/106484 A1 and WO 2006/106484 A1 (both Firmenich S A) and WO 2013/171302 A1 (Givaudan S A), each of which employ catalytic quantities of sodium or potassium methoxide bases for catalyst reformation. Indeed, the vast majority of the literature concerned with the catalytic hydrogenation of esters teaches the use of strong alkoxide bases such as these so as to activate the pre-catalyst into a sensitive metal hydride that facilitates the reduction.

There have been some reports of the synthesis and use of catalysts where an additional step has been made to prepare metal hydrides, in order that subsequent hydrogenations can then operate without the use of strong alkoxide bases. Examples of such a strategy are described by J Zhang et al. (*Angew. Chem. Int. Ed.,* 118, 1131-1133 (2006)). In this, ruthenium hydride complexes are reported to be effective ester hydrogenation catalysts under relatively mild, neutral conditions, with no additives being required.

M Ito et al. (*J. Am. Chem. Soc.,* 133, 4240-4242 (2011)) describe the use of sub-substoichiometric quantities of a potassium tert-butoxide base in the hydrogenation of chiral esters having a stereogenic centre with ruthenium-containing catalysts. In particular, the authors suggest that this may cause a reversible deprotonation in substrates having relatively acidic C—H bonds, which possibly leads to racemisation of chiral non-racemic substrates with a tertiary stereogenic centre at the alpha carbon atom. Epimerisation of such stereocentres is described as allowing an enantioselective hydrogenation by dynamic kinetic resolution.

W. Kuriyama et al. (*Adv. Synth. Catal.,* 352, 92-96 (2010)) report on how the use of a reportedly highly active ruthenium catalyst (a $RuCl_2(aminobisphosphine)_2$) could catalyse the reduction of chiral esters, but with both a considerable loss in enantiomeric excess and undesirable side reactions. In consequence, it was decided that more neutral conditions were required for the ester reductions to succeed. In view of earlier reports of the catalytic hydrogenation of ketones without addition of a base, with $RuH(\eta^1-BH_4)(bisphosphine)(diamine)$ and $RuH(\eta^1-BH_4)(aminobisphosphine)_2$ complexes, a $RuCl_2(bisphosphine)(diamine)$ was converted into the corresponding $RuH(\eta^1-BH_4)(bisphosphine)(diamine)$ by treatment of 25 equivalents of sodium borohydride. The complex was then used at relatively high catalyst loadings (such as 1 mol %).

Alternative chemistry was subsequently reported by some of the same authors (W. Kuriyama et al. (*Org. Process Res. Devel.,* 16, 166-171 (2012))) in connection with the hydrogenation of methyl (R)-lactate with a specific ruthenium catalyst to provide (R)-1,2-propanediol with high optical purity. In this publication, the methodology once again included use of a strong base (sodium methoxide). To avoid dramatic loss of optical purity (which occurred when reactions were conducted at 80° C.), use of temperatures of 30° C. and 40° C. are reported.

Similarly to the 2010 publication by W. Kuriyama et al. (supra), S Werkmeister et al. (*Angew. Chem. Int. Ed.,* 53, 8722-8726 (2014)) describe the use of a pre-activated FeH $(\eta^1-BH_4)$ complex comprising a pincer-type PNP ligand for the reduction of achiral esters to their corresponding alcohols. As with the corresponding ruthenium complexes, such activated complexes tend to involve the use of excess hydride reagents during synthesis.

Other metals that have been described in connection with catalytic hydrogenation of esters include the third row transition metals iridium and osmium. D Spasyuk et al. (*J. Am. Chem. Soc.,* 137, 3743-3746 (2015)) describe the use of specific osmium catalysts, in conjunction with a variety of bases, in the hydrogenation of unsaturated esters. The reaction is described as displaying chemoselectivity (i.e. towards the ester functionality over the carbon-carbon double bonds present in the esters that are hydrogenated).

X Yang et al. (*Chem. Sci.*, 8, 1811-1814 (2017)) report the use of an iridium hydride complex comprising a tridentate spiro pyridine-aminophosphine ligand, in combination with potassium or sodium tert-butoxide, for the asymmetric hydrogenation of racemic α-substituted lactones to chiral diols. Similarly to the chemistry described by M Ito et al. (supra), the asymmetry of the hydrogenation in view of the racemic starting material was attributed to dynamic kinetic resolution. The authors report that, in contrast to reactions involving use of potassium or sodium tert-butoxide, the use of potassium hydroxide, sodium hydroxide or potassium carbonate resulted in low yields.

As noted above, M B Widegren et al. (supra) describe the use of a hydrogenation catalyst based on a manganese complex of a chiral P,N,N ligand in the hydrogenation of esters and enantioselective hydrogenation of pro-chiral ketones. Although the use of potassium phosphate and potassium carbonate is described in connection with the reduction of ketones, all of the reported examples of ester hydrogenation involve use of potassium tert-butoxide as base.

S. Elangovan et al. (*Angew. Chem. Int. Ed.*, 55, 15364-15368 (2016)) report the use of manganese complexes stabilised by pincer-type PNP ligands, in combination with catalytic quantities of potassium tert-butoxide, for the hydrogenation of achiral esters to their corresponding alcohols.

A non-pincer-type manganese complex, stabilised by a PN ligand, is reported by R. van Putten et al. (*Angew. Chem. Int. Ed.*, 56, 7531-7534 (2017)). Yet again, the reported hydrogenation is conducted in the presence of catalytic amounts of potassium tert-butoxide. Other bases tested give much poorer, or no, conversions.

Ruthenium, iridium and osmium are rare, expensive and potentially toxic metals, and it would generally be preferable, therefore, to use catalysts based on earth-abundant, less expensive and more environmentally friendly metals, for example iron or manganese. However, as just described, such catalysts have either required pre-activation in order to allow ester hydrogenation to be effected without the use of bases, with such catalysts typically being less active and less stable, and more complicated to make, or have (as is customary in the art) been used in conjunction with very strong bases (typically with metal alkoxide salts such as potassium tert-butoxide, which is expensive and incompatible with certain substrates). However, developing new catalysts for ester (as opposed to ketone) hydrogenation, is not straightforward owing to the lower electrophilicity of the carbon atom of the carbonyl group in esters.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY OF THE INVENTION

Surprisingly, we have found that use of the specific manganese-based catalysts described herein permits hydrogenation of esters to be effected at a variety of temperatures and with a variety of solvents, but without the need to use a very strong base (in particular a metal alkoxide such as sodium methoxide, sodium tert-butoxide and potassium sodium tert-butoxide) used with other catalysts, in particular, but by no means limited to those based on ruthenium. Moreover, the surprising ability to avoid the use of strong bases in these hydrogenations means that optically active substrates susceptible to racemisation via deprotonation of relatively acidic C—H bonds, e.g. alpha to carbonyl moieties, can be subjected to hydrogenation of ester functionalities therein with at least less disruption to optical purity than corresponding reactions in which strong bases have hitherto been used. The invention is therefore of benefit to the art.

Viewed from a first aspect, therefore, the invention provides a method comprising hydrogenating an ester in the presence of (i) a base, wherein the conjugate acid of the base has a pKa from 6.4 to 14, (ii) hydrogen gas and (iii) a catalyst comprising a charged or neutral complex of formula (I):

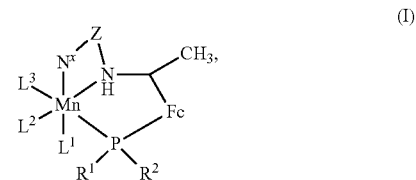

wherein:

Mn is a manganese atom or a manganese ion in oxidation state (I) to (VII);

$R^1$ and $R^2$ are each independently $C_{1-20}$hydrocarbyl or heterocyclyl moieties, optionally substituted one or more times with a substituent selected from the group consisting of halo, aliphatic $C_{1-6}$hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido;

-Fc- denotes a ferrocene (bis($\eta^5$-cyclopentadienyl)iron) moiety covalently bonded via adjacent carbon atoms of one of the two cyclopentadienyl moieties, and which may be optionally further substituted, in either cyclopentadienyl ring, one or more times with a substituent selected from the group consisting of halo, aliphatic $C_{1-6}$hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido;

—Z— is an alkylene linker of the formula —$(CH_2)_{1-6}$— in which one or more of the hydrogen atoms of the alkylene may be independently substituted with an alkyl, aryl, heteroaryl, hydroxy, nitro, amino, alkoxy, alkylthio or thiol substituent;

—$N^x$ is a nitrogen-containing amino, imino or heteroaryl moiety; and $L^1$-$L^3$ constitute one, two or three ligands in which each of $L^1$-$L^3$ independently represents a monodentate neutral or anionic ligand; or one of $L^1$-$L^3$ represents a monodentate neutral or anionic ligand and the other two of $L^1$-$L^3$ together represent a bidentate neutral or anionic ligand; or $L^1$-$L^3$ together represent a tridentate neutral or anionic ligand, wherein, when the complex of formula (I) is charged, the catalyst comprises one or more additional counterions to balance the charge of the complex.

Further aspects and embodiments of the present invention will become apparent from the detailed discussion of the invention that follows below.

DETAILED DESCRIPTION OF THE INVENTION

Throughout this specification the word "comprise", or variants such as "comprises" or "comprising", will be understood to imply the inclusion of a stated element, integer or step, or group of elements, integers or steps, but not the exclusion of any other element, integer or step, or group of elements, integers or steps.

The term "about", particularly in reference to a given quantity, is intended to encompass deviations of ±5%. For example both 0.95 and 105 are intended to fall within a range stated to be from about 1 to about 100.

According to the method of the invention, particular catalysts are used to catalyse the hydrogenation of esters in the presence of weak bases. The expression "used to catalyse" herein indicates that that the catalyst is used to promote the hydrogenation reaction, with use of molecular hydrogen ($H_2$), in a substoichiometric amount (relative to the ester substrate being hydrogenated), i.e. that the catalyst is present in an amount of less than 1 molar equivalent (100 mol %) relative to the ester.

The expression "used to catalyse" does not require that the catalyst with which the ester is contacted is the actual catalytic species, but simply that the catalyst is used in order to promote the hydrogenation reaction. The catalyst, defined as such in connection with the practice of this invention, may therefore be a so-called pre-catalyst, which may be converted to the actual catalytic species during the course of the hydrogenation reaction.

Catalysts which may be used in connection with the method of the invention can, for example, be prepared by mixing a manganese salt and additional ligand(s) appropriate to form a catalyst comprising a complex of formula (I), in the same reaction vessel in which a hydrogenation of the present invention is conducted. This is an example of an in situ preparative method. Alternatively, the catalyst may be prepared ex situ, by first forming an isolable complex, which may optionally be isolated, and then used as the catalyst in the method of the invention. Such ex situ-prepared catalysts may therefore be regarded as well-defined, the term well-defined denoting herein (as the term is used customarily in the art) a compound that has been isolated such that it is susceptible to characterisation (i.e. definition) and analysis (e.g. to determine its structure and degree of purity). In contrast, a catalyst that is not well-defined is one that is prepared without isolation from the medium (e.g. reaction medium) in which it is prepared, for example catalysts prepared in situ.

Typical substoichiometric amounts of catalysts that may be used in accordance with this invention will be in the range of about 0.001 to about 10 mol %, e.g. about 0.01 to about 5 mol %, typically about 0.05 to about 2 mol %, relative to the molar amount of the ester substrate. It will be understood that greater amounts of the catalyst will generally accelerate (i.e. promote to a greater extent) the hydrogenation reaction and that hydrogenation reactions may therefore be subject to routine optimisation by adjustment of the amount of catalyst used (as well as other features of the hydrogenation reaction described herein, for example concentration of the ester in the reaction medium) in accordance with the normal ability of the skilled person.

In connection with the present invention, unless a particular context explicitly suggests to the contrary, the following definitions apply, which are considered to confirm the general understanding of a person of skill in the art. Where the meaning of a particular functional group used herein is not expressly defined, it is intended that such a term is likewise to be understood as it would by person of normal skill in the art, typically as evidenced by the publication of the Organic Chemical Division of the International Union of Pure and Applied Chemistry entitled "Glossary of class names of organic compounds and reactive intermediates based on structure" (*Pure & Appl. Chem.*, 67(8/9), 1307-1375 (1995)).

By $C_{1-20}$hydrocarbyl is meant an aliphatic or aromatic radical comprising hydrogen atoms and from 1 and 20 carbon atoms. Where aliphatic, the hydrocarbyl may be straight-chain or branched and/or comprise one or more sites of unsaturation (e.g. one or more carbon-carbon double or triple bonds). For example, a $C_{1-6}$hydrocarbyl moiety may be a $C_{1-6}$alkyl, $C_{2-6}$alkenyl, $C_{2-6}$alkynyl or $C_{3-6}$cycloalkyl moiety. Alternatively or additionally, hydrocarbyl moieties may be cyclic or a portion of their structure may be cyclic. For example, cyclohexylmethyl and cyclohexenylmethyl are both examples of an aliphatic $C_7$hydrocarbyl.

Often, but not necessarily, hydrocarbyl moieties described herein are saturated and aliphatic, i.e. are straight-chain and/or branched, cyclic or comprise one or more cyclic portions within a straight-chain or branched architecture.

By heterocyclyl is meant a univalent group formed formally by abstraction of a hydrogen atom from any ring atom of a heterocyclic compound, which may be heteroaromatic. Typically a heterocyclyl moiety herein is based on a mono- bi- or tricyclic heterocycle, generally a monocyclic heterocycle.

By "halide" reference is being made to fluoride, chloride, bromide or iodide, typically chloride, bromide or iodide. Likewise, halo denotes fluoro, chloro, bromo or iodo, typically chloro, bromo or iodo.

Often but not necessarily, trihalomethyl denotes trifluoromethyl.

Aryl denotes a monovalent group formed formally by abstraction of one hydrogen atom from an aromatic moiety (used synonymously herein with the term arene, to denote a mono- or polycyclic aromatic hydrocarbon). Analogously, heteroaryl denotes a monovalent group formed formally by abstraction of one hydrogen atom from a heteroaryl moiety (used synonymously herein with the term heteroarene, to denote a mono- or polycyclic heteraromatic hydrocarbon).

Aryl groups are typically monocyclic groups, unless the context specifically dictates to the contrary, for example phenyl, although bicyclic aryl groups, such as naphthyl, and tricyclic aryl groups, such as phenanthryl and anthracyl, are also embraced by the term aryl. References to aromatic groups herein are to be similarly interpreted, i.e. as denoting monocyclic aromatic groups absent an express indication to the contrary.

As known to those skilled in the art, heteroaromatic moieties are derived formally from aromatic moieties by substitution of one or more (generally one or two) heteroatoms, typically O, N or S, in place of one or more carbon atoms together with any hydrogen atoms attached thereto. Illustrative heteroaromatic moieties include pyridine, furan, pyrrole and pyrimidine. Further examples of heteroaromatic rings include pyridazine (in which two nitrogen atoms are adjacent in an aromatic 6-membered ring); pyrazine (in which two nitrogens are 1,4-disposed in a 6-membered aromatic ring); pyrimidine (in which two nitrogen atoms are 1,3-disposed in a 6-membered aromatic ring); or 1,3,5-triazine (in which three nitrogen atoms are 1,3,5-disposed in a 6-membered aromatic ring).

Heteroaryl groups are typically monocyclic groups, unless the context specifically dictates to the contrary, for example pyridyl, although bicyclic heteroaryl groups, for example such as indolyl, are also embraced by the term heteroaryl. References to heteroaromatic groups herein are to be similarly interpreted, i.e. as denoting monocyclic heteroaromatic groups absent an express indication to the contrary.

By amino is meant herein a group of the formula —N($R^4$)$_2$, wherein each $R^4$ independently denotes hydrogen or $C_{1-6}$hydrocarbyl or heteroaryl, or the two $R^4$ moieties together form an alkylene diradical, derived formally from an alkane from which two hydrogen atoms have been abstracted, typically from terminal carbon atoms, whereby to form a ring together with the nitrogen atom of the amine. Where $R^4$ is other than hydrogen (including those embodiments where the two $R^4$ moieties together form an alkylene diradical), one or more of its carbon atoms may be optionally substituted one or more times with one or more substituents independently selected from the group consisting of halo, $C_{1-6}$hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido, more typically within the optional substituents are selected from the group consisting of halo, $C_{1-6}$hydrocarbyl, trihalomethyl, aryl and heteroaryl.

Typically, except wherein —$N^x$ is amino, amino herein denotes —N($R^4$)$_2$, wherein each $R^4$ independently denotes hydrogen or $C_{1-6}$hydrocarbyl. Often, except where —$N^x$ is amino, amino denotes —$NH_2$, or simple monoalkyl- or dialkylamino moieties (for example the dialkylamino moiety dimethylamino (—N($CH_3$)$_2$)).

References to amino herein are also to be understood as embracing within their ambit quaternised or protonated derivatives of the amines resultant from compounds comprising such amino groups. Examples of the latter may be understood to be salts such as hydrochloride salts.

Alkoxy (synonymous with alkyloxy) and alkylthio moieties are of the formulae —$OR^5$ and —$SR^5$ respectively, wherein $R^5$ is a saturated aliphatic hydrocarbyl group, typically a $C_{1-6}$alkyl or $C_{3-6}$cycloalkyl group, optionally substituted with one or more substituents selected from the group consisting of halo, aryl and heteroaryl.

By carboxylate, sulfonate and phosphate are meant herein the functional groups —$CO_2^-$, —$SO_3^-$ and —$PO_4^{2-}$ respectively, which may be in their protonated forms.

By formyl is meant a group of formula —C(H)O.

By ester is meant a functional group comprising the moiety —OC(=O)—.

By acyl is meant the functional group of formula —C(O)$R^5$, wherein $R^5$ is as hereinbefore defined. Analogously, thioacyl denotes a functional group of the formula —C(O)$R^5$, again wherein $R^5$ is as hereinbefore defined.

By carbamido is meant herein a functional group, either of formula —$NHCOR^5$ or of formula —$CONHR^5$, wherein $R^5$ is as hereinbefore defined. Analogously, sulfonamido denotes a functional group, either of formula —$NHSO_2R^5$, or of formula —$SO_2NHR^5$, wherein $R^5$ is as hereinbefore defined.

Where a ligand is stated to be monodentate, it is capable of coordinating (i.e. to the manganese centre) through one donor site. Where a ligand is bidentate, it is capable of coordinating through two discrete donor sites.

The catalyst used in accordance with the invention is characterised by comprising a complex of formula (I), as described herein. The nature of the complex is discussed in detail below.

Although (without wishing to be bound by theory) the catalytic species that constitutes the starting point of the catalytic hydrogenation reaction may be one comprising a manganese ion in oxidation state (I), it is well-known in the field of transition metal catalysis that initial pre-catalysts may be presented with a transition metal centre in a variety of oxidation states. These may be converted, with appropriate oxidation or reduction of the transition metal (here a manganese) atom or ion to a catalytically active species during the course of the reaction being catalysed, i.e. with any necessary oxidation or reduction of the manganese centre. Appropriate oxidation or reduction of the manganese atom or ion may be achieved, for example, with a suitable reducing or oxidising agent, or reactive ligand.

Two examples of the uses of manganese (II) pre-catalysts in which the manganese is present in oxidation state (II), different to that of the active catalytic species, are described by V Vasilenko et al. (*Angew. Chem. Int. Ed.*, 56, 8393-8397 (2017)) in connection with the hydroboration of ketones and X Ma et al. (*ACS Omega*, 2, 4688-4692 (2017)) in connection with the hydrosilylation of aryl ketones.

Moreover, it is well known that manganese (0) species such as $Mn_2(CO)_{10}$ undergo oxidation to the desired Mn species. Indeed, Nguyen et al. report on such an oxidation with amino ligand to produce reduction catalysts (*ACS Catal.*, 7, 2022-2032 (2017)).

While there is no necessity to employ a higher oxidation state Mn precursor, reduction of high oxidation state manganese (e.g. in the context of oxidation reagents) to Mn(II) is well-known. Even simple alkoxide salts can reduce higher valent metal salts to the desired low valent species, see JH Docherty et al. (*Nature Chemistry*, 9, 595-600 (2017)). Accordingly, with the appropriate reducing agents, manganese-containing compounds in oxidation states>(II) may be expected to be of use in conjunction with the present invention.

The complex of formula (I) may therefore comprise a manganese atom or a manganese ion in oxidation state (I) to (VII), typically a manganese ion, often a manganese ion in oxidation state (I) or (II), and very often a manganese ion in oxidation state (I).

Although in accordance with the present invention we find the use of the commercially available manganese (I) salt bromopentacarbonylmanganese (I) ($Mn(CO)_5Br$) convenient, it will be understood that other commercially available (for example manganese (0) carbonyl ($Mn_2(CO)_{10}$)) or readily accessible manganese compounds may also be used to prepare complexes for use in the method of the invention.

As is evident from the structure of the complex of formula (I), $R^1$ and $R^2$ are substituents of the phosphine moiety within the tridentate ligand of formula $R^1(R^2)PFcC(CH_3)N(H)ZN^x$ within the complex of formula (I). As will be understood by those skilled in the art, there is generally the possibility to significantly vary within such ligands, inter alia, the substituents $R^1$ and $R^2$ of such phosphino moieties. Routine variation of these, for example through variation in steric bulk around and/or electronic influences upon the phosphorus atoms of such phosphino moieties, allows the skilled person to optimise such ligands in catalysts and complexes comprising these for any given reaction.

For example, the $R^1$ and $R^2$ ligands may be aliphatic or aromatic (or heteroaromatic) with significant substitution possible, without disrupting the function of catalysts comprising such moieties in their role as hydrogenation catalysts. Moreover, there exists a large variety of commercially available or otherwise easily accessible phosphorus-containing reagents from which $R^1$- and $R^2$-containing ligands may be prepared. Still further, it has been demonstrated in the art both that a variety of relevant ligands can be made and that complexes comprising these (including ferrocene-based PNN tridentate ligands of the formula $R^1(R^2)PFcC(CH_3)N(H)ZN^x$ defined in formula (I) herein) may be used in the context of catalytic hydrogenation reactions. For example, H Nie et al. (Tetrahedron: Asymmetry., 24, 1567-1571 (2013) and Organometallics, 33, 2109-2114 (2014)) describe variation in the substitution of phenyl groups within the terminal diphenylphosphino moieties of such ligands, e.g. with a variety of alkyl substitution.

When constructing diphenylphosphino-substituted ferrocenes, Nie et al. describe introduction of the diphenylphosphino moiety via selective lithiation ortho to a substituent corresponding to the —C(CH$_3$)N— fragment within the tridentate ligand of formula $R^1(R^2)PFcC(CH_3)N(H)ZN^x$, within the complex of formula (I) defined herein, followed by treatment with a variety of chlorodiaryphosphines. In view of the huge variety of analogous electrophilic chlorophosphines that are available to the skilled person, it is well within his routine ability to prepare related ligands having other substituents on the phosphorus atom, for example optionally substituted aliphatic, heteroaryl and other aryl $R^1$ and $R^2$ moieties, for example to allow access to dialkylphosphino-containing ligands such as diethylphosphino- and ditert-butylphosphino-.

As detailed in the experimental section below, we have synthesised a ligand of formula $R^1(R^2)PFcC(CH_3)N(H)ZN^x$ in which ZN is 2-pyridylmethyl by reaction between a N,N-dimethyl-1-ethylamino-substituted ferrocene in the presence of acetic anhydride and 2-picolylamine (2-aminomethylpyridine). We have also synthesised a ligand of formula $R^1(R^2)PFcC(CH_3)N(H)ZN^x$ in which $ZN^x$ is 4-dimethylaminopyridin-2-ylmethyl by reaction between a 1-ethylamino-substituted ferrocene with 4-dimethylamino-2-formylpyridine in the presence of sodium borohydride. Furthermore, as an example to illustrate the accessibility of complexes of formula (I), we note that the commercial availability of alternatively substituted ferrocenes, sold under the trade name PFA from Solvias AG, Switzerland, makes straightforward the synthesis of alternative $R^1$- and $R^2$ substituted ligands of formula $R^1(R^2)PFcC(CH_3)N(H)ZN$ by substitution of a different commercially available ferrocene to (S)-1-[Bis(4-methoxy-3,5-dimethylphenyl) phosphino]-2-[(R)-1-(DMA)ethyl]ferrocene or ((R)-1-[(S)-1-(dimethylamino)ethyl]-2-(diphenylphosphino) ferrocene) the use of which is described herein.

In particular, the following ferrocenes are commercially available from Solvias (in which DMA denotes dimethylamino):

(S)-1-[(R)-1-(DMA)ethyl]-2-(diphenylphosphino)ferrocene;
(R)-1-[(S)-1-(DMA)ethyl]-2-(diphenylphosphino)ferrocene;
(R)-1-[Bis(4-methoxy-3,5-dimethylphenyl)phosphino]-2-[(S)-1-(DMA)ethyl]ferrocene;
(S)-1-(Difuranylphosphino)-2-[(R)-1-(DMA)ethyl]ferrocene;
(R)-1-(Difuranylphosphino)-2-[(S)-1-(DMA)ethyl]ferrocene;
(S)-1-[Bis[3,5-bis(trifluoromethyl)phenyl]phosphino]-2-[(R)-1-(DMA)ethyl]ferrocene;
(R)-1-[Bis[3,5-bis(trifluoromethyl)phenyl]phosphino]-2-[(S)-1-(DMA)ethyl]ferrocene;
(S)-1-(Dicyclohexylphosphino)-2-[(R)-1-(DMA)ethyl]ferrocene; and
(R)-1-(Dicyclohexylphosphino)-2-[(S)-1-(DMA)ethyl]ferrocene.

These may be used to provide a complex for use in accordance with the present invention in which the $R^1R^2P$-Fc-CH(Me)-NH— moiety of the complex of formula (I) is:

(S)-1-[(R)-1-(HN)ethyl]-2-(diphenylphosphino)ferrocene;
(R)-1-[(S)-1-(HN)ethyl]-2-(diphenylphosphino)ferrocene;
(S)-1-[Bis(4-methoxy-3,5-dimethylphenyl)phosphino]-2-[(R)-1-(HN)ethyl]ferrocene;
(R)-1-[Bis(4-methoxy-3,5-dimethylphenyl)phosphino]-2-[(S)-1-(HN)ethyl]ferrocene;
(S)-1-(Difuranylphosphino)-2-[(R)-1-(HN)ethyl]ferrocene;
(R)-1-(Difuranylphosphino)-2-[(S)-1-(HN)ethyl]ferrocene;
(S)-1-[Bis[3,5-bis(trifluoromethyl)phenyl]phosphino]-2-[(R)-1-(HN)ethyl]ferrocene;
(R)-1-[Bis[3,5-bis(trifluoromethyl)phenyl]phosphino]-2-[(S)-1-(HN)ethyl]ferrocene;
(S)-1-(Dicyclohexylphosphino)-2-[(R)-1-(HN)ethyl]ferrocene; or
(R)-1-(Dicyclohexylphosphino)-2-[(S)-1-(HN)ethyl]ferrocene, i.e. in which the dimethylamino (DMA) moiety is replaced with the NH moiety within the tridentate ligands of formula $R^1(R^2)PFc$-CH(Me)-N(H)ZN$^x$ described herein.

Although the present invention is exemplified herein with the use of a chiral catalyst, this was because of the commercial availability of this catalyst in non-racemic form. Because the hydrogenation described herein does not generate a new stereogenic centre (in contradistinction to the hydrogenation of prochiral ketone substrates), there is neither a disadvantage nor an advantage in using mixtures of enantiomers of chiral ligands in the preparation of complexes of formula (I).

Although a wide range of $R^1$ and $R^2$ are both accessible synthetically, and useful in accordance with the hydrogenation of the present invention, according to particular embodiments of the present invention $R^1$ and $R^2$ are each independently optionally substituted $C_{1-10}$hydrocarbyl or monocyclic heteroaryl moieties. For example, and as noted already, $R^1$ and $R^2$ moieties may be dialkylphosphino moieties such as diethylphosphino or di-tert-butylphosphino.

According to more particular embodiments, $R^1$ and $R^2$ are each independently optionally substituted $C_{5-10}$cycloalkyl, monocyclic aryl or monocyclic heteroaryl moieties, for example optionally substituted phenyl, furanyl or cyclohexyl moieties. Both phenyl, furanyl or cyclohexyl moieties, and in particular phenyl moieties, as well as other $C_{1-20}$hydrocarbyl or heterocyclyl possibilities for $R^1$ and $R^2$, may be independently unsubstituted or substituted with one or more substituents selected from the group consisting of $C_{1-6}$alkyl, $C_{1-6}$alkyloxy, halo, and trihalomethyl. According to still more particular embodiments where there is substitution, this is often with one or more $C_{1-6}$alkyl and/or $C_{1-6}$alkyloxy substituents.

According to specific embodiments, moieties which can independently constitute $R^1$ and $R^2$ are 4-methoxy-3,5-dimethylphenyl, phenyl, 3,5-dimethylphenyl, 4-methoxy-3,5-di-tert-butylphenyl, 3,5-di(tert-butyl)phenyl, furanyl or cyclohexyl. According to these and other $R^1$ and $R^2$ moieties, both $R^1$ and $R^2$ will generally, but not necessarily, be the same moiety.

Analogously to the flexibility of access, synthetically, to a variety of $R^1$ and $R^2$ moieties, the skilled person has access to complexes of formula (I) comprising a large variety of Fc moieties, with relevant reagents both available commercially (see supra with respect to the reagents commercially available from Solvias), but also which may be incorporated within complexes of formula (I) using methodology of which the skilled person is well aware. In this regard, TD Appleton et al. (*J. Organomet. Chem.*, 279(1-2), 5-21 (1985)) describe ready functionalisation of the cyclopentadiene rings of ferrocene.

According to particular embodiments of the invention, one or more carbon atoms of either cyclopentadienyl ring of the ferrocene moiety Fc may be substituted with one or more halo and/or $C_{1-6}$alkyl substituents, in addition that is to the inherent substitution of the Fc moiety at those carbon atoms of one of its cyclopentadienyl rings, which connect Fc with the remainder of the complex of formula (I). According to still more particular embodiments of the invention, however, neither cyclopentadienyl ring of the Fc moiety within formula (I) is substituted (other than the inherent substitution through the ferrocene's points of connectivity with the remainder of the complex of formula (I) that is).

Access to the CH(Me) moiety within the complex of formula (I) that is adjacent to the Fc moiety is readily available to the skilled person owing to the commercial availability of what is known in the art as Ugi's amine (N,N-dimethyl-1-ferrocenylethylamine), available as either enantiomer.

N,N-dimethyl-1-ferrocenylethylamine may be reacted, using methodology described for example by H Nie et al. (supra), to access the corresponding 2-phosphino derivatives (which may incorporate the $R^1$ and $R^2$ moieties described herein), by selection of an appropriate chlorophosphine as described above. The N,N-dimethylamino moieties of the resultant 2-phosphino derivatives may then be transformed to the corresponding unsubstituted amino moieties before effecting reductive amination with an appropriate $N^x$-containing aldehyde (wherein $N^x$ is as defined herein), as also described by H Nie et al. (supra) and described herein to allow access to ligands of formula $R^1(R^2)$PFc-CH(Me)-NH—Z—$N^x$ described herein.

Alternatively, as described herein, the unsubstituted amino moieties may be reacted with an amine of formula $N^x$—Z—$NH_2$, wherein N and Z are as defined herein, in order to access the ligands of formula $R^1(R^2)$PFc-CH(Me)-NH—Z—$N^x$. It will be understood that variation of either the aldehyde or amine of formula $N^x$—Z—$NH_2$ will allow access to variations of the —Z—$N^x$ terminus of the ligands of formula $R(R^2)$PFc-CH(Me)-NH—Z—$N^x$. More generally, a wide variety of compounds of formula $R(R^2)$PFc-CH(Me)-LG, wherein LG is a leaving group such as acetate or $NMe_2$, are accessible to the skilled person. These may then be converted to the ligands of formula $R^1(R^2)$PFc-CH(Me)-NH—Z—$N^x$ through the methodologies described herein. Accordingly, it is readily within the normal ability of the skilled person to access ligands of formula $R^1(R^2)$PFc-CH(Me)-NH—Z—$N^x$.

Still further, additional ways and strategies for incorporating into the ferrocene a structurally diverse array of substituents may be appreciated with reference to HU Blaser et al. (*Topics in Catalysis*, 19(1), 3-16 (2002)), which provides further teaching of assistance to the skilled person, in particular with respect to variation of the CH(Me)-NH—Z—$N^x$ portion of the ligands of formula $R^1(R^2)$PFc-CH(Me)-NH—Z—$N^x$.

In the complexes of formula (I), —Z— is an alkylene linker of the formula —$(CH_2)_{1-6}$— in which one or more of the hydrogen atoms of the alkylene may be independently substituted with an alkyl, aryl, heteroaryl, hydroxy, nitro, amino, alkoxy, alkylthio or thiol substituent. Access to variations in such linkers may be achieved, for example by reacting compounds of formula $R^1(R^2)$PFc-CH(Me)-LG, as described above, for example in which LG=$NMe_2$, with different primary amines having Z groups other than methylene (—$CH_2$—) as is present in 2-picolylamine. (Analogously, it will be appreciated that access to different $N^x$ groups may additionally (to varying the Z group that is) or alternatively be achieved by reacting compounds of formula $R(R^2)$PFc-CH(Me)-LG with different primary amines having $N^x$ groups other than the 2-pyridyl present in 2-picolylamine).

An alternative strategy to vary the —Z— groups in the complexes of formula (I) may be appreciated by consultation of C-J Hou and X-P Hu (*Org. Lett.*, 18, 5592-5595 (2016)) in which the authors describe ligands of formula $R^1(R^2)$PFc-CH(Me)-NH—Z—$N^x$ wherein the —Z— moiety may be a substituted methylene linker (for example by reaction of 1-(2-pyridinyl)ethylmethanesulfonate with a compound of formula $R^1(R^2)$PFc-CH(Me)-$NH_2$ (whereby to provide a methyl-substituted methylene linker —Z—)); or by condensing various 2-acylpyridines with the same compound of formula $R^1(R^2)$PFc-CH(Me)-$NH_2$ followed by hydrogenation of the resultant Schiff bases (whereby to provide a series of substituted methylene linkers —Z— in which the substituent corresponds to the R group in the 2-acylpyridines of formula 2-PyC(=O)R). (Analogously, it will be appreciated that access to N groups different to 2-pyridyl may additionally (to varying the Z group that is) or alternatively be achieved by reacting compounds of formula $R^1(R^2)$PFc-CH(Me)-$NH_2$ with derivatives of the 1-(2-pyridinyl)ethylmethanesulfonate and the 2-acylpyridines having $N^x$ groups other than 2-pyridyl).

According to particular embodiments of the invention, —Z— is of the formula —$(CH_2)$—, —$(CHR^3)$— or —$(CH_2)_2$—, wherein $R^3$ is an alkyl, aryl, heteroaryl, hydroxy, nitro, amino, alkoxy, alkylthio or thiol substituent. According to particular embodiments of the invention, —Z— is of the formula —$(CH_2)$—, —$(CHR^3)$— or —$(CH_2)_2$—, wherein $R^3$ is a $C_{1-6}$alkyl substituent or phenyl optionally substituted one or more times with $C_{1-6}$alkyl and/or halo. According to other embodiments, —Z— is of the formula —$(CH_2)$—, —$(CHR^3)$— or —$(CH_2)_2$—, wherein $R^3$ is methyl or phenyl optionally substituted one or more times with $C_{1-6}$alkyl and/or halo.

Often (but not necessarily in view of the discussion herein of the availability of substituted alkylene linkers of formula —Z—), —Z— is unsubstituted. For example, —Z— may be of the formula —$(CH_2)$— or —$(CH_2)_2$—, often —$(CH_2)$—.

Various ways in which the N moiety within the ligands of formula $R^1(R^2)$PFc-CH(Me)-NH—Z—$N^x$ may be varied have been described above. In addition, however, it may be noted that W Wu et al. (*Org. Lett.*, 18, 2938-2941 (2016)) illustrate a further strategy for constructing such ligands, wherein —Z— is methylene and $N^x$ is a substituted oxazolyl by reacting a primary amine of formula $R^1(R^2)$PFc-CH(Me)-$NH_2$ with a variety of substituted chloromethyloxazoles. It will be readily understood that both the —Z— and $N^x$ moieties may be varied according to such a synthetic strategy.

From the discussion herein, it will be appreciated that there is no particular limitation on the architecture of the nitrogen atom-containing moiety $N^x$ in the complex of formula (I). This notwithstanding, the nitrogen atom of $N^x$ according to particular embodiments of the invention is within a heterocyclyl ring, which is optionally substituted one or more times with one or more substituents independently selected from the group consisting of amino, halo, $C_{1-6}$hydrocarbyl, trihalomethyl, aryl, heteroaryl, hydroxy, nitro, alkoxy, alkylthio, carboxylate, sulfonate, phosphate, cyano, thio, formyl, ester, acyl, thioacyl, carbamido and sulfonamido.

According to some embodiments, the heterocyclyl ring comprising $N^x$ is optionally substituted one or more times with one or more substituents independently selected from the group consisting of amino, halo, $C_{1-6}$alkyl and aryl. According to these and other embodiments of the invention, the heterocyclyl ring comprising $N^x$ is a pyridyl, indolyl, quinolinyl, isoquinolinyl, pyrimidinyl, pyrrolyl, pyrrolidinyl, pyrrolinyl, oxazolyl, isooxazolyl, imidazolyl, pyrazolyl, quinoxalinyl, pyridazinyl, triazolyl, triazinyl, imidazolidinyl or oxadiazolyl ring, for example a pyridyl, indolyl, quinolinyl, isoquinolinyl, pyrimidinyl, pyrrolyl, oxazolyl, isooxazolyl, imidazolyl, pyrazolyl, quinoxalinyl, pyridazinyl, or triazolyl ring; and/or a monocyclic heteroaryl ring. According to particular embodiments, the heterocyclyl ring comprising $N^x$ is an optionally substituted pyridyl ring, for example a pyridyl ring optionally substituted one or more times with an amino substituent, which is substituted with Z at a carbon atom adjacent to the nitrogen atom of the pyridyl ring. The amino substituent is often a tertiary amino, substituted with two $C_{1-6}$alkyl substituents. Typically, the two $C_{1-6}$alkyl substituents are the same and are selected from the group consisting of methyl, ethyl, propyl, iso-propyl, n-butyl, sec-butyl, isobutyl and tert-butyl. According to still more particular embodiments, —$N^x$ is 4-dimethylamino-pyridin-2yl or 2-pyridyl.

As well as the tridentate ligand of formula $R^1(R^2)$PFc-CH(Me)-NH—Z—$N^x$, within the complexes of formula (I), the complex additionally comprises the ligands $L^1$-$L^3$. These may constitute one, two or three ligands depending on whether one of them is a bidentate or a tridentate ligand: each of $L^1$-$L^3$ independently may represent a monodentate neutral or anionic ligand; one of $L^1$-$L^3$ may represent a monodentate neutral or anionic ligand and the other two of $L^1$-$L^3$ together represent a bidentate neutral or anionic ligand; or $L^1$-$L^3$ together may represent a tridentate neutral or anionic ligand.

The nature of the $L^1$-$L^3$ ligands is not of particular significance to the present invention: any convenient neutral or anionic ligands may be used, which may be monodentate, bidentate or tridentate, typically monodentate or bidentate. The ligands $L^1$-$L^3$ may be, for example, selected from the group consisting of (i) neutral ligands selected from the group consisting of carbon monoxide, nitrogen monoxide, amines, ethers, thioethers, sulfoxides, nitriles, for example acetonitrile, isocyanides, for example methyl isocyanide, phosphorus-containing ligands based on either phosphorus (III) or phosphorus (V) and water; and (ii) anionic ligands selected from the group consisting of halides, alkoxides, anions of carboxylic, sulfonic and phosphoric acids, amido ligands, thiolates, phosphides, cyanide, thiocyanate, isothiocyanate, and enolate ions, for example acetylacetonate. Where $L^1$-$L^3$ together represent a tridentate ligand, this is often, but not necessarily neutral. An example of a neutral tridentate ligand is diglyme.

According to particular embodiments of this invention $L^1$-$L^3$ constitute three ligands selected from neutral monodentate ligands. According to these and other embodiments, $L^1$-$L^3$ may be the same. For example, $L^1$-$L^3$ may constitute three carbon monoxide ligands.

Where the complex of formula (I) is charged, the catalyst comprises one or more additional counterions to balance the charge of the complex, i.e. the charge resultant from the complex formed by the manganese centre Mn, and the ligand or ligands $L^1$-$L^3$ and $R^1(R^2)$PFc-CH(Me)-NH—Z—$N^x$. As with the ligand or ligands $L^1$-$L^3$, the nature of any such additional counterions is not of particular importance to the working of the present invention. Where these are present, they may be, for example, selected from the group consisting of halides, tetraarylborates, $SbF_6^-$, $SbCl_6^-$, $AsF_6^-$, $BF_4^-$, $PF_6^-$, $ClO_4^-$ and $CF_3SO_3^-$, optionally wherein the tetraarylborate ligands are selected from the group consisting of $[B\{3,5\text{-}(CF_3)_2C_6H_3\}_4]^-$, $[B\{3,5\text{-}(CH_3)_2C_6H_3\}_4]^-$, $[B(C_6F_5)_4]^-$ and $[B(C_6H_5)_4]^-$, for example where the tetraarylborate ligand is $[B\{3,5\text{-}(CF_3)_2CH_3\}_4]^-$, which is known as tetrakis(3,5-bis(trifluoromethyl)phenyl)borate (BARF)).

According to particular embodiments of the invention, the complex has a single positive charge (for example resultant from the manganese centre being a manganese ion in oxidation state (I) and the ligand or ligands $L^1$-$L^3$ being three neutral monodentate ligands, for example three carbon monoxide ligands) and the catalyst further comprises one halide or tetrarylborate counteranion. According to still more particular embodiments of such catalysts, the counteranion is bromide or BARF.

As will be recognised, the complexes of formula (I) exhibit chirality, both on account of the stereogenic centre adjacent to the Fc moiety (which bears the methyl group depicted within the compounds of formula (I)), and also on account of the planar chirality resultant from the 1,2-connectivity to the remainder of the complex of formula (I), from one of the two cyclopentadienyl rings of the Fc moiety. As has also been alluded to, however, since no stereogenic centre is formed in consequence of the hydrogenation of an ester functionality, it will be understood that the invention may be operated using catalysts comprising mixtures of any stereoisomers (for example enantiomers or diastereomers) of complexes of formula (I), for example racemic mixtures of enantiomeric complexes and catalysts comprising these.

For example, according to particular embodiments of the invention, the catalyst has one of the formulae:

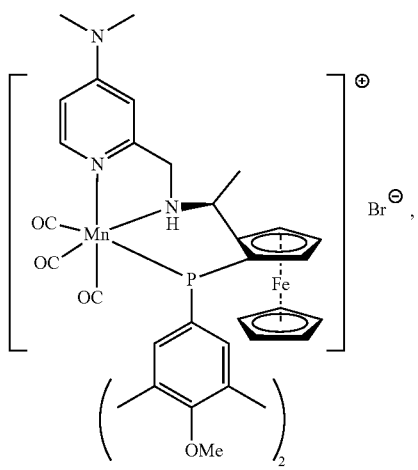

-continued
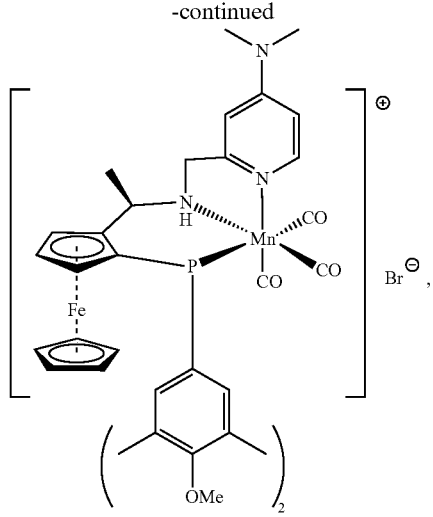
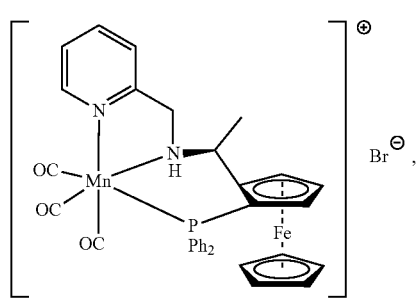
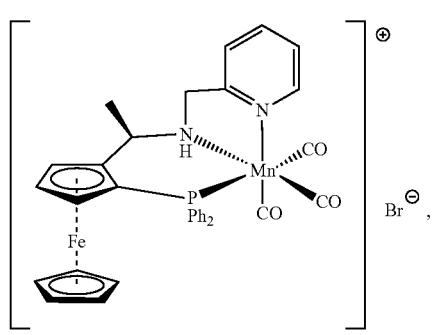
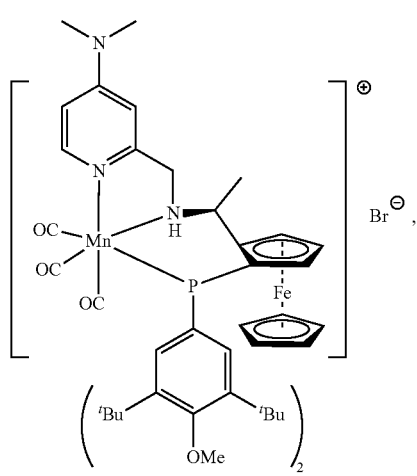
-continued
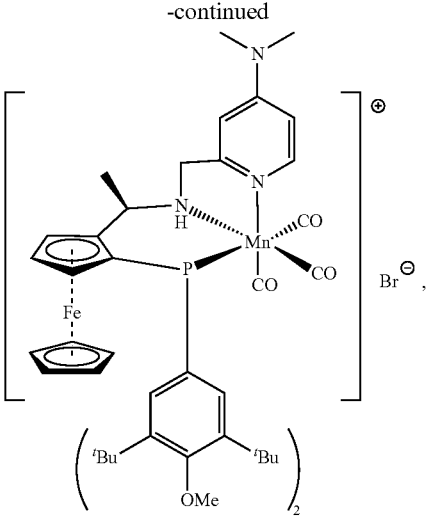
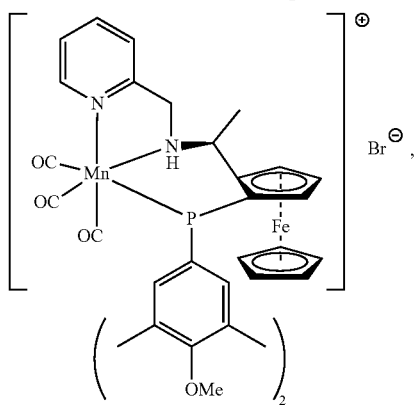
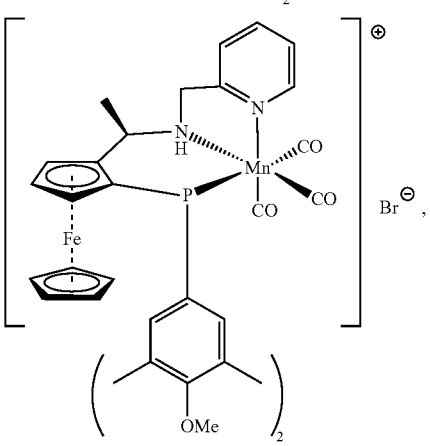
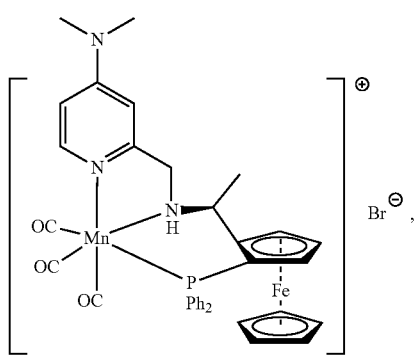

-continued
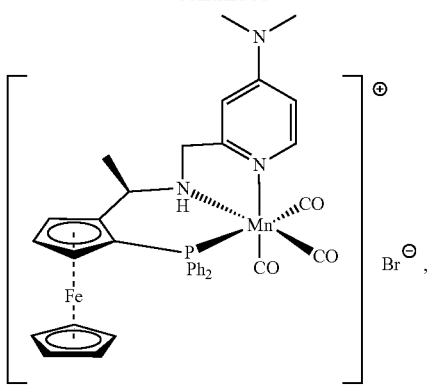
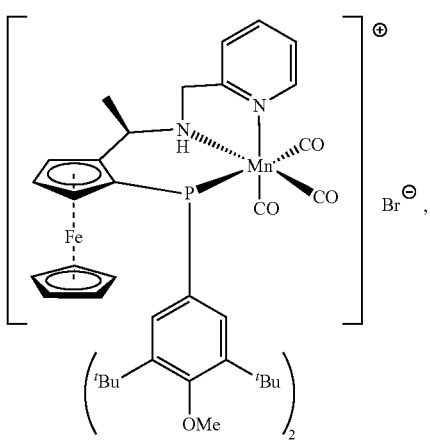
wherein $^t$Bu is tert-butyl.
However, the catalyst may equally be a mixture of each enantiomeric pair, for example a racemic mixture, or mixture of other catalysts comprising complexes of formula (I).
Typically, the catalyst has one of the formulae:
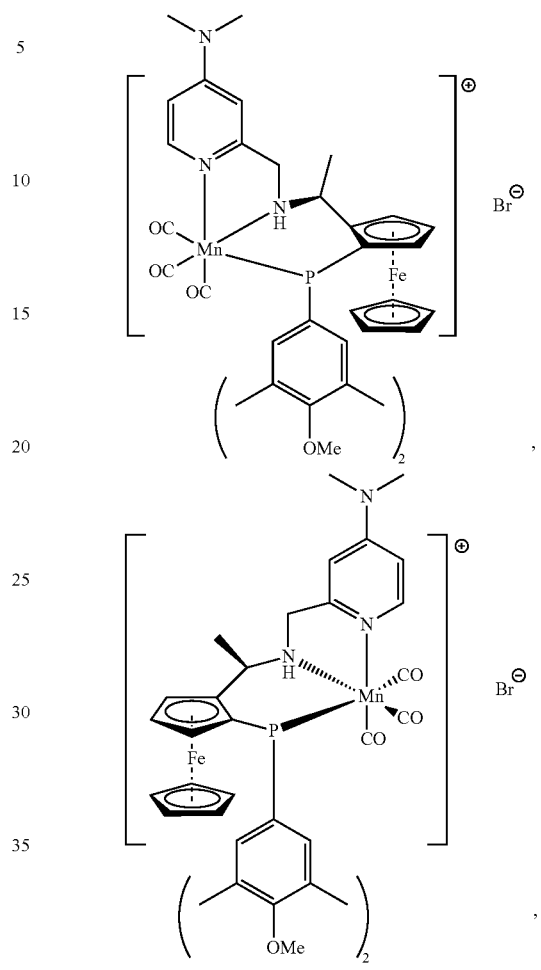
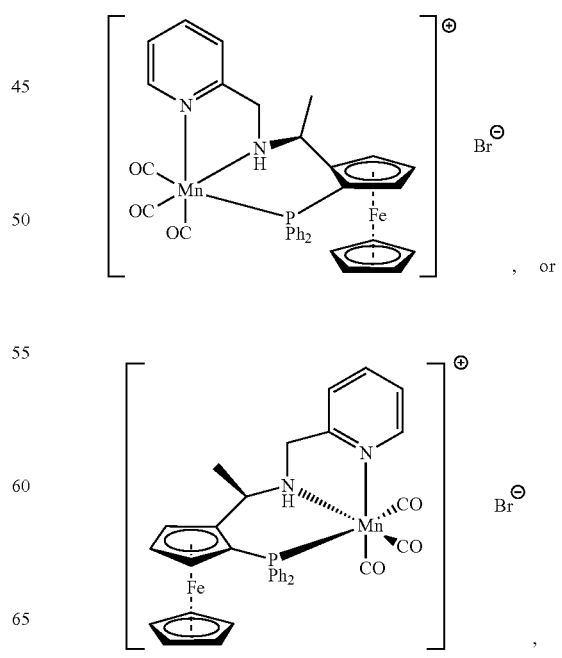

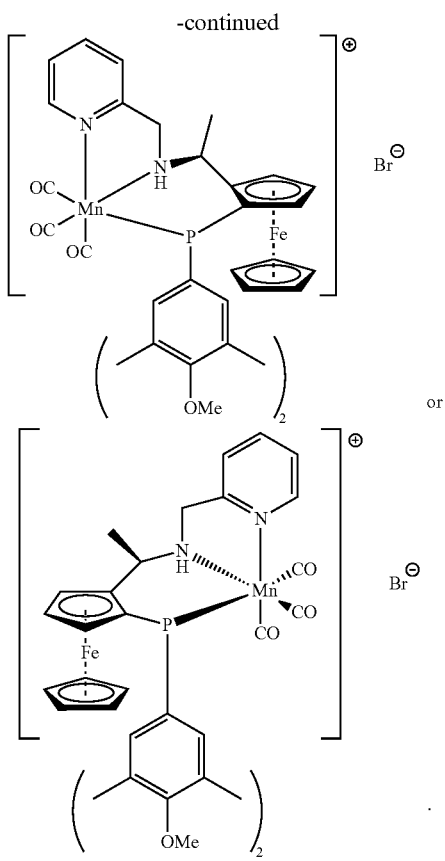

As already alluded to above, catalysts useful in connection with the present invention can, for example, be prepared by mixing an appropriate manganese salt, which may or may not comprise the ligand or ligands $L^1$-$L^3$, and additional ligand(s), e.g. a ligand of the formula $R^1(R^2)$PFc-CH(Me)-NH—Z—$N^x$, suitable to form a catalyst comprising a complex of formula (I), in the same reaction vessel in which a hydrogenation of the present invention is conducted. Alternatively, an optionally well-defined catalyst may be prepared ex situ, as briefly described above. It is readily within the ability of those of normal skill in the art to prepare such catalysts, using the guidance herein, including with reference to the experimental section and prior art with which the skilled person is aware, including that cited herein.

It will be readily appreciated by those skilled in the art that, if desired, recognised methods of immobilisation of catalysts of formula (I) herein can be used to generate heterogeneous catalysts, for example by absorption onto a suitable solid support or reacted with such a support to form a covalently bound ligand or catalyst.

A characteristic feature of the method of the present invention involves the use of a base wherein the conjugate acid of the base has a pKa from 6.3 to 14. For the avoidance of doubt, these pKa values relate to determinations conducted in water, at 25° C., for the reaction BH$^+$ ⇌ H$^+$+ B, wherein BH$^+$ denotes the conjugate acid of the base concerned, as described in the CRC *Handbook of Chemistry and Physics*, 91$^{st}$ edition, 2010, Dissociation Constants of Organic Acids and Bases, and Dissociation Constants of Inorganic Acids and Bases, and the references cited therein. Accordingly, where the base used is potassium bicarbonate (KHCO$_3$), for example, the conjugate acid is carbonic acid (H$_2$CO$_3$); where the base used is potassium carbonate (K$_2$CO$_3$), for example, the conjugate acid is bicarbonate (HCO$_3^-$). For further avoidance of doubt, the pKa of water at 25° C. is defined herein, as is generally recognised in the art, as being 14.0. Accordingly, for example, the pKa of the conjugate acid of both sodium hydroxide and potassium hydroxide (i.e. water) is 14.0.

In some texts, the pKa of water is indicated as being 15.74 (higher than that of methanol (15.50) for reasons explained in detail as being incorrect by TP Silverstein et al. (*J. Chem. Educ.*, 94(6), 690-695 (2017)).

For the avoidance of any doubt, however, the present invention does not embrace, for use as the base in accordance with the method of the invention, any metal alkoxide, such as sodium methoxide, potassium tert-butoxide and the like. Accordingly, viewed from a second aspect, the invention provides a method comprising hydrogenating an ester in the presence of (i) a base other than a metal alkoxide, (ii) hydrogen gas and (iii) a catalyst comprising a charged or neutral complex of formula (I) as defined in connection with the first aspect of the invention, and elsewhere herein.

According to some embodiments of the invention (i.e. in accordance with both its first and second aspects), the base is selected from the group consisting of a lithium, beryllium, sodium, magnesium, potassium, calcium or cesium carbonate, phosphate, hydroxide or bicarbonate (i.e one of these four salts of these six metals) or a mixture thereof, e.g. is selected from the group consisting of a lithium, sodium, magnesium, potassium, calcium or cesium carbonate, phosphate, hydroxide or bicarbonate, or a mixture thereof. According to more specific embodiments of the invention (i.e. in accordance with both the first and second aspects), the base is selected from the group consisting of potassium carbonate, potassium phosphate, potassium hydroxide, sodium carbonate, cesium carbonate, sodium hydroxide, lithium carbonate, lithium hydroxide, calcium hydroxide, potassium bicarbonate, sodium bicarbonate and lithium bicarbonate.

According to particular embodiments of the invention (i.e. again in accordance with both the first and second aspects), the conjugate acid of the base has a pKa from 10.3 to 14. Such pKas exclude, for example, bicarbonates.

Although we have found that use of metal bicarbonates tends to provide less efficient hydrogenation conversions than when using, for example, metal carbonates, phosphates or hydroxides, we have demonstrated that hydrogenation is nevertheless achievable with the use of such bases and the skilled person will recognise that extensive conversion may be increased by routine modifications of reaction protocols, for example by increasing the concentrations of such bases, catalyst loading, hydrogen pressure, temperature, duration of reaction or any combination of these modifications.

According to still more particular embodiments of the invention (once again in accordance with both the first and second aspects), the base is selected from the group consisting of potassium carbonate, potassium phosphate, potassium hydroxide, sodium carbonate, cesium carbonate, sodium hydroxide, lithium carbonate, lithium hydroxide, and calcium hydroxide, for example the group consisting of potassium carbonate, potassium phosphate, potassium hydroxide, sodium carbonate and cesium carbonate.

According to other embodiments of the first and second aspects of the invention, the base used in accordance with these methods of hydrogenation may be a tertiary amine, typically of the formula N(C$_{1-6}$alkyl)$_3$, in which each alkyl group need not necessarily be the same. Examples of tertiary amines that may be used include triethylamine, N,N-dimethylamine and N,N-diisopropylethylamine (also known as Hünig's base).

Viewed from a third aspect, the invention provides a method comprising hydrogenating an ester in the presence of (i) a base, which is a lithium, beryllium, sodium, magnesium, potassium calcium or cesium carbonate, phosphate, hydroxide or bicarbonate, or a tertiary amine, for example of the formula $N(C_{1-6}alkyl)_3$ defined above (ii) hydrogen gas and (iii) a catalyst comprising a charged or neutral complex of formula (I) as defined in connection with the first aspect of the invention, and elsewhere herein.

According to particular embodiments of the third aspect of the invention, the base is selected from the group consisting of potassium carbonate, potassium phosphate, potassium hydroxide, sodium carbonate, cesium carbonate, sodium hydroxide, lithium carbonate, lithium hydroxide, calcium hydroxide, potassium bicarbonate, sodium bicarbonate and lithium bicarbonate, for example wherein the base is selected from the group consisting of potassium carbonate, potassium phosphate, potassium hydroxide, sodium carbonate, cesium carbonate, sodium hydroxide, lithium carbonate, lithium hydroxide, and calcium hydroxide, and, according to particular embodiments, wherein the base is selected from the group consisting of potassium carbonate, potassium phosphate, potassium hydroxide, sodium carbonate and cesium carbonate.

The methods of the invention, as is typical for hydrogenation reactions, are conducted in the presence of hydrogen gas, under pressure. Generally the pressure at which the reactions are conducted is in the range of about 1 bar (100 kPa) to about 100 bar (10,000 kPa), for example from about 20 bar (2,000 kPa) to about 80 bar (8,000 kPa), although higher or lower pressures may on occasion be convenient.

The reactions may be carried out in any convenient solvent as may be suitable for the substrate for the reaction (i.e. the ester). In certain embodiments, it may be convenient to conduct hydrogenations in the absence of solvent. Any of the commonly encountered solvents in organic chemistry can potentially be utilised. However, solvents comprising ketone or ester functionalities, such as acetone or ethyl acetate respectively, are preferably avoided.

Typical solvents for use in the present invention include simple alcohols, such as $C_{1-10}$hydrocarbyl alcohols, often saturated aliphatic $C_{2-8}$alcohols, for example, ethanol, isopropanol and tert-butanol; polyvalent alcohols such as ethylene glycol, propylene glycol, 1,2-propanediol and glycerol; ethers, for example tetrahydrofuran (THF) 1,4-dioxane, methyl tert-butyl ether, cyclopentyl methyl ether; aliphatic and aromatic hydrocarbon solvents, for example $C_{5-12}$alkanes, benzene, toluene and xylene and halogenated (typically chlorinated) hydrocarbon solvents, for example dichloromethane and chlorobenzene, or mixtures thereof, in particular, mixtures of alcohols, for example ethanol or isopropanol, and hydrocarbon solvents such as hexanes, xylenes (i.e. isomeric mixtures) or toluene. According to particular embodiments, methanol is not used as a solvent in the present invention.

Conveniently, however, hydrogenation reactions of the present invention can typically be conducted in $C_{1-10}$hydrocarbyl alcohols alone (i.e. in which the only solvent is the alcohol, or there is minimal (e.g. less than 10 vol %, more typically less than 5 vol %) contamination with other liquid, for example water), in particular in ethanol or isopropanol. According to some embodiments of the invention, therefore the solvent for the reaction is isopropanol. According to other embodiments, the solvent is ethanol.

It will be understood that the precise conditions for any given hydrogenation reaction may be varied within the routine ability of those of normal skill in the art. Thus, the concentration of catalyst and hydrogen pressure may typically be varied within the ranges already discussed. Operating temperatures that may be used typically vary from about –20° C. to about 200° C., often from about 20° C. to about 120° C., for example from about 50° C. to about 110° C.; and durations of reaction may vary from about 5 minutes to about 36 hours, for example from about 1 hour to about 24 hours or from about 2 hours to about 18 hours.

Suitable amounts of base that may be used can likewise be determined by the skilled person. One of the advantages of the present invention is that the costs of many of the bases are significantly lower than those of metal alkoxides. Another advantage is the greatly reduced sensitivity of the basis described herein to water. The use of larger amounts of bases in connection with the present invention is therefore less problematic than with metal alkoxides. Examples of suitable amounts of base to use may vary from about 0.1 mol % to about 1000 mol %, with respect to the ester reactant, for example from about 1 mol % and about 100 mol %, e.g. from about 5 and about 50 mol %. It may on occasion be convenient or advantageous to use greater quantities of base, however, for example up to 2000 mol % or more. Combinations of more than one base may also be used.

As noted above, the present invention is premised, in part, on the ability to effect hydrogenation of esters at a variety of temperatures and with a variety of solvents, but without the need to use a very strong base when doing so. Esters that may therefore serve as the substrate for the hydrogenation reactions in accordance with the present invention are therefore not particularly limited. Typically, however, the ester functionality is connected to one or more hydrocarbyl moieties (for the avoidance of doubt, esters that may be hydrogenated in accordance with the scope of the present invention include cyclic esters (i.e. lactones)), optionally comprising amino or halo functionality. According to particular embodiments, the hydrocarbyl moieties to which the ester functional group is connected do not comprise an unsaturated aliphatic portion, although they may comprise aromatic or heteroaromatic moieties in addition to one or more saturated aliphatic portions.

A particular advantage resultant from the avoidance of strong bases in hydrogenation reactions in accordance with the present invention is the ability to hydrogenate optically active substrates, for example those susceptible to racemisation via deprotonation of relatively acidic C—H bonds, e.g. alpha to carbonyl moieties, with at least less disruption to optical purity than corresponding reactions in which strong bases have hitherto been used.

According to particular embodiments of the present invention, therefore, the ester is optically active. According to more particular embodiments, the ester comprises a stereogenic centre adjacent to its carbonyl group. When hydrogenating optically active esters in accordance with the present invention, the enantiomeric excess within the optically active ester submitted to the hydrogenation is typically maintained, or diminished no more than about 10% by the hydrogenation (i.e. the Δ e.e. is 0 or less than about 10%), for example by no more than about 5%. Advantageously, we have found that the Δ e.e. in accordance with the present invention is frequently <0%.

According to a specific embodiment of the present invention, the ester hydrogenated is the commercially available (e.g. from Sigma-Aldrich) lactone sclareolide, which has the formula:

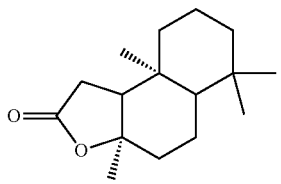

The CAS #for sclareolide is [564-20-5] and it is known by a number of names, including (+)-Norambreinolide, (3aR)-(+)-Sclareolide, (R)-(+)-sclareolide, (3aR,5aS,9aS,9bR)-decahydro-3a,6,6,9a-tetramethyl-naphtha[2,1-b]furan-2(1H)-one, 3a,4,5,5aα,6,7,8,9,9a,9bα-decahydro-3aβ,6,6,9aβ-tetramethyl-naphtho[2,1-b]furan-2(1H)-one and [3aR-(3aα,5aβ,9aα,9bβ)]-decahydro-3a,6,6,9a-tetramethyl-naphtho[2,1-b]furan-2(1H)-one.

Sclareolide may be used in the synthesis of ambroxide, by hydrogenation of the ester to form the corresponding diol (known under a number of synonyms including ambradiol, which can then be dehydrated to form ambroxide:

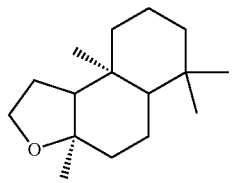

which is highly valued in perfumery as a sensualising fixative. The use of hydrogenations of the present invention in conjunction with ambroxide manufacture therefore represents a fourth aspect of the present invention. This fourth aspect provides a method of making ambroxide comprising hydrogenating sclareolide in accordance with any of the 1$^{st}$ to 3$^{rd}$ aspect of the invention and thereafter cyclising the resultant diol (ambradiol) so as to provide ambroxide.

The skilled person is well aware of methods for conversion of ambradiol into ambroxide. In particular there is described in WO 2017/068401 A1 (Universidad Michoacana De San Nicolás De Hidalgo)) a method for synthesising ambroxide from an extract of the plant *Ageratina jocotepecana* in which numerous suitable methods for converting ambradiol into ambroxide are described, both within the application itself and with reference to inter ala U.S. Pat. No. 5,463,089 (first-named inventor DHR Barton), published US Patent Application of publication number US 2010/0248316 A1 (first-named inventor LH Steenkamp), published Spanish Patent Application of publication number ES 2044780 (Universidad de Granada), published Spanish Patent Application of publication number ES 2195777 (Universidad de Granada), EP 0204009 A1 (Fritzsche Dodge & Olcott Inc.), EP 0165458 A2 (T. HASEGAWA COMPANY, LTD.), RC Cambie et al. (*Aust. J. Chem.*, 24 583-591 & 2365-2377 (1971)), published Russian Patent Application of publication number SU 988817 (INST KHIMII AN MSSR), U.S. Pat. No. 59,274,134 (first-named inventor K Bruns), and SI Martinez-Guido et al. (*ACS Sustainable Chem. Eng.*, 2(10), 2380-2390 (2014)). Any of these known methods may be used to cyclise ambradiol so as to provide ambroxide.

Each and every patent and non-patent reference referred to herein is hereby incorporated by reference in its entirety, as if the entire contents of each reference were set forth herein in its entirety.

The non-limiting examples below more fully illustrate the embodiments of this invention.

General Experimental Procedures

The preparation of solutions for the use in catalytic reactions were carried out under either argon or nitrogen atmospheres. All glassware was used oven dried or flame dried and cooled under vacuum before use. Solvents were degassed either by bubbling argon or nitrogen through the solvent for at least 1 hour prior to use or freeze-pumped-thawed before use. Unless otherwise noted all precursor chemicals were purchased from Sigma-Aldrich, Acros, Alfa Aesar, Strem or TCI and used as received (excepts when further degassed as stated above). Room temperature or ambient temperature refers to the temperature range 15-25° C. Heating the reaction mixtures were effected by either an oil bath or a Drysyn heating block. Reported temperature is the oil bath or heating block temperature and not internal temperature unless stated and was measured using a contact thermometer (PT-1000). In vacuo refers to either the use of a Heidolph Laborota 4001 rotary evaporator or the use of a high-vacuum line. Analytical thin layer chromatography (TLC) was carried out on pre-coated plastic plates (Kieselgel 60 F254 silica). TLC visualisation was carried out using a UV lamp (254 nm) or using a 1% potassium permanganate aqueous solution. Flash silica chromatography was performed using Kieselgel 60 silica.

$^1$H, $^{13}$C, $^{31}$P, $^{19}$F NMR was carried out using either a Bruker Avance 300 (300 MHz for $^1$H, 75 MHz for $^{13}$C, 121 MHz for $^{31}$P and 282 MHz for $^{19}$F), a Bruker Avance II 400 (400 MHz $^1$H, 100 MHz 13C, 161 MHz $^{31}$P and 376 MHz for $^{19}$F) or a Bruker Ultrashield 500 (500 MHz $^1$H, 125 MHz $^{13}$C, 201 MHz $^{31}$P and 470 MHz for $^{19}$F). NMR analyses were carried out at room temperature in the deuterated. The chemical shifts are quoted as parts per million (ppm). Coupling constants, J, are quoted in Hz. Multiplicities are indicated by: s (singlet), d (doublet), t (triplet), q (quartet) and m (multiplet). The abbreviation "br" is used to denote broad peak shape.

Infrared spectra were recorded on a Shimadzu IRAffinity-1 using Pike attenuated total reflectance (ATR) accessory. Peaks are reported as weak (w), medium (m) or strong (s). The abbreviation "br" denote a broad peak shape and "sh" denote a sharp peak shape. All units are reported in cm-1.

Mass spectrometric (m/z) data were acquired by electrospray ionisation (ESI) or electron impact (EI) either at the University of St Andrews Mass Spectrometry facility (using Micromass LCT spectrometer or Micromass GCT spectrometer) or at the EPRSC National Mass Spectrometry Service Centre, Swansea (using Orbitrap nano-ESI, Finnigan MAT 900 XLT or Finnigan MAT 95 XP). Values are reported as a ratio of mass to charge in Daltons. Optical rotations were measured on a Perkin Elmer 341 polarimeter using a 1 ml cell with a 1 dm path length at room temperature using the sodium D-line, and a suitable solvent that is reported along with the concentration (c=g/100 ml). HPLC analysis has been determined using a Varian Prostar operated by Galaxie workstation PC software.

Synthesis of (S$_c$,R$_p$)—N-2-Picolyl-1-(2-Diphenylphosphino)ferrocenylethylamine (1)

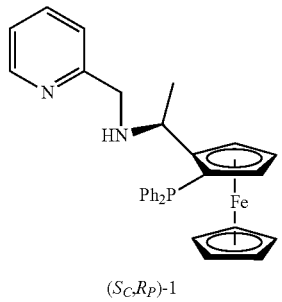

(S$_C$,R$_P$)-1

To the readily available (Sc, Rp)-N,N-dimethyl-1-[2-(diphenylphosphino) ferrocenyl]ethylamine (209 mg, 0.47 mmol)[8] was added degassed acetic anhydride (152 µL, 1.59 mmol). The reaction mixture was heated to 90° C. and the solution eventually became homogeneous. The mixture was held at the reaction temperature until TLC analysis (EtOAc:Heptane, 20:80, Et$_3$N deactivated) showed full conversion (typically 2-3 h). The solution was cooled to room temperature and isopropanol (551 µL) was added. To this solution, degassed 2-picolylamine (985 µL, 9.55 mmol) in isopropanol (276 µL) was added and the reaction mixture was heated at 60° C.-70° C. for 5 days, under argon atmosphere until TLC analysis (EtOAc:Heptane, 20:80, Et$_3$N deactivated) showed the reaction to be complete. The reaction mixture was concentrated in vacuo and the crude product was purified by column chromatography (EtOAc: Hexane, 50:50, Et$_3$N deactivated silica) to give an orange oil which was crystallised in hexane to give the product as orange crystals (106.4 mg, 0.211 mmol, 45%).

$^1$H-NMR (CDCl$_3$) δ: 8.31 (1H, d, J 4.9, NC$_{(pyridine)}$H), 7.59-7.48 (2H, m, C$_{Ar}$H), 7.43-7.26 (5H, m, C$_{Ar}$H), 7.26-7.21 (2H, m, C$_{Ar}$H), 7.18-7.11 (3H, m, C$_{Ar}$H), 7.03-6.94 (1H, m, NC$_{(pyridine)}$HC$_{(pyridine)}$H), 6.55 (1H, d, J 7.8, NHCH), 4.55 (1H, br s, C$_5$H$_3$), 4.32 (1H, t, J 2.5, C$_5$H$_3$), 4.26-4.17 (1H, m, NHCH), 4.02 (5H, S, C$_5$H$_5$), 3.83 (1H, S, C$_5$H$_3$), 3.64 (2H, d, J 2.1, CArCH$_2$NH) and 1.57 (3H, d, J 6.0, CHCH$_3$);

$^{13}$C-{$^1$H}-NMR (CDCl$_3$) δ: 159.7 (s, NC$_{(pyridine)}$CH$_2$), 148.7 (s, NC$_{(pyridine)}$), 140.0 (d, J 10.04, C$_{Ar}$, PPh$_2$), 137.2 (d, J 9.12, C$_{Ar}$, PPh$_2$)), 136.1 (s, C$_{(pyridine)}$), 135.0 (d, J 20.96, 2×C$_{Ar}$H, PPh$_2$), 132.6 (d, J 18.88, 2×C$_{Ar}$H, PPh$_2$), 129.1 (s, C$_{(pyridine)}$), 128.3 (d, J 6.31, 2×C$_{Ar}$H, PPh$_2$), 128.1 (d, J 6.31, 2×C$_{Ar}$H, PPh$_2$), 128.0 (s, C$_{(pyridine)}$), 121.6 (s, C$_{Ar}$H, PPh$_2$), 121.4 (s, C$_{Ar}$H, PPh$_2$), 97.5 (d, J 25.52, C, RC$_5$H$_3$), 75.1 (d, J 8.11, C, C$_5$H$_3$P), 71.3 (d, J 4.0, CH, C$_5$H$_3$), 69.7 (s, C$_5$H$_5$), 69.5 (d, J 4.0, CH, C$_5$H$_3$), 69.2 (s, CH, C$_5$H$_3$), 52.1 (s, HNCH$_2$), 51.3 (d, J 7.4, NCH) and 19.5 (s, CHCH$_3$);

$^{31}$P{$^1$H}-NMR (CDCl$_3$) δ: −25.1 (PPh$_2$).

MS: (ES+) 527.13 ((M+Na)$^+$, 33%), 397.08 ((M-picolylamine), 100%);

IR (KBr): ν$_{max}$/cm$^{-1}$ (KBr) 3736 (w), 3438 (m), 3050 (m), 2925 (m), 1588 (m), 1568 (m), 1494 (m), 1476 (s), 1454 (s), 1374 (m), 1310 (w), 1239 (m), 1170 (m), 1139 (m), 1107 (s), 1042 (m), 1025 (m), 996 (m), 823 (m), 780 (m), 746 (s), 702 (s) cm-1

[α$_D^{20}$]: +285.2 (c 0.25, chloroform).

Alternative Synthesis of (1)

An alternative synthesis of (1) based on a previously published procedure (H Nie et al. (supra)) could also be used and is detailed below:

Synthesis of (Sc,Rp)-1-(2-Diphenylphosphino)ferrocenylethylamine, 1-Int (Sc, Rp)-N,N-dimethyl-1-(2-diphenylphosphino)ferrocenylethylamine (2.42 g, 5.48 mmol, 1.0 equivalents) in a round bottom flask was added acetic anhydride (10 mL) and the mixture heated to 100° C. and held for 2 h. After cooling to ambient temperature excess acetic anhydride was removed in vacuo. To the residue was added a methanol/THF (1:1) mixture (48 mL) and aqueous ammonium hydroxide (10 mL). The formed biphasic mixture was heated to 60° C. under an argon atmosphere and held for 3 h, then cooled back to ambient temperature. Volatiles were removed in vacuo and the residue extracted with dichloromethane (3×20 mL). The solutions were pooled, dried over magnesium sulfate, filtered through a cannula equipped with a filter, and concentrated. The product (Sc, Rp)-1-(2-diphenylphopshino)ferrocenylethylamine was purified by silica chromatography, where the silica was deactivated with triethylamine, using a n-hexane/ethyl acetate gradient (4/1 to 2/1) to give the intermediate as an orange solid (1.6 g, 3.87 mmol, 70% yield).

$^1$H-NMR (CDCl$_3$) δ: 7.58-7.54 (2H, m, C$_{Ar}$H), 7.41 (3H, m, C$_{Ar}$H), 7.26 (5H, m, C$_{Ar}$H), 4.46 (1H, br s, C$_5$H$_3$), 4.30 (1H, m, C$_5$H$_3$), 4.25-4.21 (1H, m, NHCH), 4.04 (5H, s, C$_5$H$_5$), 3.79 (1H, s, C$_5$H$_3$), 1.46 (3H, d, J=7.2 Hz, CHCH$_3$), 1.45 (2H, s, —NH$_2$)

$^{13}$C{$^1$H}-NMR (CDCl$_3$) δ: 140.0 (d, J$_{PC}$=9.7 Hz, Ar—C), 137.11 (d, J$_{PC}$=10.0 Hz, Ar—C), 134.90 (d, J$_{PC}$=20.3 Hz, Ar—C$^{ipso}$—P), 132.76 (d, J$_{PC}$=17.1 Hz, Ar—C), 129.12 (Ar—C), 128.38 (Ar—C), 128.33 (Ar—C), 128.17 (Ar—C), 128.11 (Ar—C), 100.35 (d, J$_{PC}$=24.4 Hz, Fc-C$^{ipso}$—P), 74.7 (d, J$_{PC}$=8.3 Hz, Fc-C), 71.24 (Fc-C), 69.56 (Fc-C), 69.0 (Fc-C), 68.22 (Fc-C), 45.30 (d, J$_{PC}$=8.6 Hz, Fc-C), 26.93 (Fc-CH(CH$_3$)—N), 22.84 (Fc-CH(CH$_3$)—N), $^{31}$P{$^1$H}-NMR (CDCl$_3$) δ: −24.5 ppm MS: (ES+) calculated for [C$_{24}$H$_{25}$FeNP]$^+$ 414.1069; found 414.1063. Fits with previously published data (G Sheldrick, Acta Crystallogr., Sect. C, 71, 3-8 (2015))

(Sc, Rp)-1-(2-diphenylphosphino)ferrocenylethylamine (1.06 g, 2.56 mmol, 1.0 equivalents) was dissolved in degassed, dry methanol (15 mL) in a round bottom flask at ambient temperature. Pyridine-2-carboxaldehyde (0.30 mL, 3.08 mmol, 1.2 equivalents) was added to the flask and the mixture stirred at ambient temperature for 16 h, after which time the imine precipitated out. Sodium borohydride (194 mg, 5.13 mmol, 2.0 equivalents) was added to the mixture and the resulting clear solution was stirred at 40° C. for 1.5 h, then cooled to ambient temperature and concentrated to dryness. The crude material was taken up in dichloromethane (20 mL) and washed with saturated aqueous sodium bicarbonate solution (15 mL). The aqueous layer was extracted with dichloromethane (20 mL). The combined solutions were dried over magnesium sulfate, filtered through a cannula equipped with a filter, and concentrated. The product was purified by silica chromatography (The silica was deactivated using triethylamine) using a gradient of n-hexane/ethyl acetate (5/1 to 1/1 to 0/1) to give 1 as an orange-yellow solid (0.94 g, 1.86 mmol, 73% yield). Analytical data was found to be identical to the reported above using the other synthetic route to compound (1).

Synthesis of Manganese Complex $(S_C,R_P)$-2

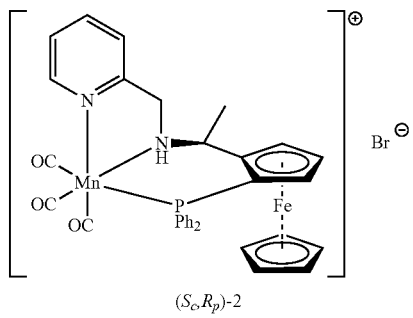

$(S_C,R_P)$-2

N-2-Picolyl (Sc, Rp)-1-(-2-diphenylphosphino)ferrocenylethylamine (280 mg, 0.56 mmol, 1.2 equivalents) was added to pentacarbonylbromomanganese (I) (128 mg, 0.47 mmol, 1.0 equivalents) in a round bottom flask at ambient temperature. Degassed toluene (10 mL) was added and the mixture was heated to reflux and kept at that temperature for 16 h. The mixture was cooled to ambient temperature and concentrated to dryness. The crude material was dissolved in methylene chloride, filtered to remove insoluble material and the product precipitated by addition of n-hexane, collected by filtration and washed with n-hexane and to give the desired product as an orange powder (203 mg, 0.28 mmol, 60% yield). The product was found to be contaminated with traces of paramagnetic material giving broad NMR peaks. Residual solvents (toluene and n-hexane) was found to be hard to remove even after extended drying time under high-vacuum (<0.3 mmHg) at >70° C. The solubility in most deuterated solvents were found to be very limited showing a higher amount of more soluble impurities than actually present. $^1H$-$^1H$ COSY and $^1H$-$^{13}C$-HSQC assisted in the assigning of peaks.

$^1$H-NMR (128 scans, Acetone-$d_6$) δ: 8.50 (1H, br s, Py-H), 8.02 (2H, m, Py-H), 7.79-7.28 (4H, m, Ar—H), 7.25-7.15 (residual toluene), 6.97 (4H, app d, Ar—H), 6.77 (3H, app. d., Ar—H), 5.57 (1H, br s, Fc-CH(CH$_3$)—N), 4.97 (1H, br s, Fc-H), 4.80 (1H, br s, Fc-H), 4.58 (1H, br s, Fc-H), 4.48 (1H, br s, NH), 4.30 (1H, m, Fc-H Py-CH$_2$—N), 3.85 (5H, br s, Fc-H), 3.72 (1H, m, Py-CH$_2$—N), 2.33 (residual toluene) 1.78 (3H, br s, Fc-CH(CH$_3$)—N), 1.52 (residual hexane), 1.29 (n-hexane)

$^{13}$C{$^1$H}-NMR (1024 scans, Acetone-$d_6$) δ: 159.97 (Ar—C), 152.70 (Ar—C), 140.30 (Ar—C), 140.03 (Ar—C), 137.05 (Ar—C), 136.12 (Ar—C), 136.29 (Ar—C), 134.42 (d, $J_{PC}$=, 10.3 Hz, Ar—$C^{ipso}$—P), 130.37 (Ar—C), 130.29 (Ar—C), 127.95 (Ar—C), 127.87 (Ar—C), 127.50 (d, $J_{PC}$=10.3 Hz, Ar—$C^{ipso}$—P), 124.46 (Ar—C), 120.22 (Ar—C), 92.25 (d, $J_{PC}$=22.2 Hz, Fc-$C^{ipso}$—P), 72.4 (Fc-C), 71.30 (Fc-C), 70.64 (Fc-C), 70.32 (Fc-C), 65.30 (Py-CH$_2$—N), 56.60 (Fc-CH(CH$_3$)—N), 54.52 (DCM), 48.65 (Fc-CH(CH$_3$)—N), 20.33 (toluene), 14.81 (n-hexane), CO not observed.

$^{31}$P-NMR (128 scans, Acetone-$d_6$) δ: 90.1 (br s) ppm

IR (ATR): 3199.91 (w), 3053.3 (w), 2358.9 (m), 2341.6 (m), 1921.0 (s), 1842.0 (s), 1712.8 (m), 1481.3 (m), 1433.1 (m), 1361.7 (w), 1232.5 (w), 1220.9 (w), 1163.1 (w), 1093.6 (m), 1051.2 (w), 999.1 (w), 829.4 (w), 758.02 (m) cm$^{-1}$

HRMS: (ESI positive): expected [C$_{33}$H$_{29}$FeMnN$_2$O$_3$P]$^+$: 643.0640, found: 643.0634

CHN: calculated for [C$_{33}$H$_{29}$BrFeMnN$_2$O$_3$P]: C, 54.80%, H, 4.04%, N, 3.87%; Found C, 54.73%; H, 4.05%; N, 3.94%.

Manganese complex 2, with a bromide counterion, may be converted to the corresponding BARF and iodide salts by reaction with Na[BARF] and sodium iodide respectively.

Compound (2) was used as the catalyst in subsequent hydrogenation examples.

Table 1 immediately below summarises the results of the following hydrogenation reactions (described thereafter):

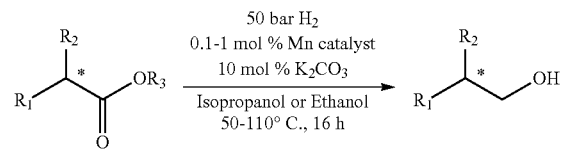

TABLE 1

| Example No | Substrate | Catalyst load (mol %)$^a$ | T (° C.) | Conversion (%) | isolated yield (%) | e.e. product (%) | Δ e.e. (%) |
|---|---|---|---|---|---|---|---|
| 1 | MeO-naphthyl-CH(CH₃)-C(O)OEt | 1.0 | 50 | 99 | 90 | 98.0 | −1.8 |
| 2 | Ph-CH(Et)-C(O)OEt | 1.0 | 110 | 99 | 90 | 98.0 | −1.0 |

TABLE 1-continued

| Example No | Substrate | Catalyst load (mol %)[a] | T (° C.) | Conversion (%) | isolated yield (%) | e.e. product (%) | Δ e.e. (%) |
|---|---|---|---|---|---|---|---|
| 3 | ethyl 3-phenylbutanoate (β-methyl, S-config) | 1.0 | 50 | 99 | 96 | 99.0 | 0 |
| 4 | benzyl 2-(dibenzylamino)-3-methylbutanoate | 1.0 | 110 | 99 | 75 | 99.8 | 0 |
| 5 | ethyl 2-(dibenzylamino)-3-phenylpropanoate | 1.0 | 110 | 99 | 66 | 99.8 | 0 |
| 6 | benzyl 2-(dibenzylamino)pent-4-enoate | 1.0 | 50 | 99 | 76 | 98.0 | 0 |
| 7 | sclareolide | 0.1* | 90 | 99 | 75 | >99 | 0 |
| 8 | benzyl 2-(dibenzylamino)-3-(1H-indol-3-yl)propanoate | 1.0 | 110 | 99 | 93 | 99.8 | 0 |
| 9 | ethyl (S)-2-(4-isobutylphenyl)propanoate | 1.0 | 50 | 99 | 96 | 98.5 | −0.5 |
| 10 | ethyl (S)-2-(4-chlorophenyl)-3-methylbutanoate | 1.0 | 50 | 99 | 91 | 96.0 | −1 |

[a] 10 mol % base for all experiments

EXAMPLES OF HYDROGENATION

Example 1: (S)-2-(6-methoxynaphthaene-2-yl)propan-1-ol (S)-ethyl naproxen (500 mg, 1.94 mmol, 1 equiv., 99.8% ee) and 1-methylnaphthalene (~50 μL, internal standard), manganese catalyst (14 mg, 0.019 mmol, 0.01 equiv.) and potassium carbonate (27 mg, 0.19 mmol, 0.1 equiv.) was added to a glass insert containing a stirring bar and the insert put in an autoclave fitted with a vacuum/gas inlet and a charging port. The vessel was sealed and evacuated and refilled with argon. This was repeated twice. Degassed isopropanol (6.3 mL) was added through the charging port and the autoclave was pressurised with hydrogen gas (50 bar) and vented to the atmosphere. This was repeated twice. The pressure was set to 50 bar using hydrogen gas and the autoclave sealed and placed in a pre-heated oil bath (50° C.)

and the stirring as set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by hexane/ethyl acetate (1/1) to give the (S)-2-(6-methoxynaphthalene-2-yl)propan-1-ol as a white solid (450 mg, 90%).

$^1$H-NMR (CDCl$_3$) δ: 7.74 (2H, t, J=8.9 Hz, Ar—H), 7.64 (1H, s, Ar—H), 7.37 (1H, d, J=7.7 Hz, Ar—H), 7.16 (2H, m, Ar—H), 3.94 (3H, s, —OC$\underline{H}_3$), 3.80 (2H, d, J=7.1 Hz, —C$\underline{H}_2$OH), 3.12 (1H, m, C$\underline{H}$(CH$_3$)—), 1.38 (3H, d, J=7.2 Hz, —C$\underline{H}_3$)

$^{13}$C-{$^1$H}-NMR (CDCl$_3$) δ: 157.23 ($\underline{C}_{Ar}$—OCH$_3$), 138.63 ($\underline{C}_{Ar}$), 133.55 ($\underline{C}_{Ar}$), 129.11 ($\underline{C}_{Ar}$), 129.03 ($\underline{C}_{Ar}$), 127.24 ($\underline{C}_{Ar}$), 126.27 ($\underline{C}_{Ar}$), 125.93 ($\underline{C}_{Ar}$), 118.93 ($\underline{C}_{Ar}$), 105.58 ($\underline{C}_{Ar}$), 68.66 (—O$\underline{C}$H$_3$), 55.33 (—$\underline{C}$H$_2$OH), 42.39 (Ar$\underline{C}$H (CH$_3$)), 17.66 (—$\underline{C}$H$_3$)

[α$_D^{20}$]: −19.1 (c. 1.00, CHCl$_3$)

Chiral analysis was performed using a Chiralcel OD-H column using n-hexane/isopropanol (96/4) mobile phase, flow 1.0 mL/min; t$_R$ (S-enantiomer, major): 17.0 min; t$_R$ (R-enantiomer, minor): 18.4 min, e.e. 98%.

Example 2: (R)-2-phenylbutan-1-ol (R)-ethyl 2-phenylbutyrate (200 mg, 1.04 mmol, 1 equiv., 99.0% ee), manganese catalyst (7.5 mg, 0.001 mmol, 0.01 equiv.), potassium carbonate (14 mg, 0.10 mmol, 0.1 equivalents) and 1-methylnaphthalene (~50 μL, internal standard) was added to a microwave vial containing a stirring bead. The vial was sealed and evacuated and refilled with argon. This was repeated twice. Degassed isopropanol (2.4 mL) was added and the vial septum as pierced with 2×18G needles and placed in a stainless-steel autoclave under argon atmosphere. The vessel was pressurised with hydrogen gas (50 bar) and vented to the atmosphere. This was repeated twice. The pressure was set to 50 bar using hydrogen gas and the autoclave sealed and placed in a pre-heated oil bath (50° C.) and the stirring as set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by hexane/ethyl acetate (1/1) to give the (R)-2-phenylbutan-1-ol as a colourless oil (140 mg, 90%).

$^1$H-NMR (CDCl$_3$) δ: 7.36 (2H, m, Ph-H), 7.24 (3H, m, Ph-H), 3.78 (2H, m, C$\underline{H}_2$OH), 2.72 (1H, m, PhC$\underline{H}$(C$_2$H$_5$)CH$_2$OH), 1.78 (1H, m, C$\underline{H}_2$CH$_3$), 1.61 (1H, m, C$\underline{H}_2$CH$_3$), 0.86 (3H, t, J=7.5 Hz, —C$\underline{H}_3$)

$^{13}$C-{$^1$H}-NMR (CDCl$_3$) δ: 142.25 ($\underline{C}_{Ar}$), 128.64 ($\underline{C}_{Ar}$), 128.12 ($\underline{C}_{Ar}$), 126.73 ($\underline{C}_{Ar}$), 67.36 (—$\underline{C}$H$_2$OH), 50.52 (Ph$\underline{C}$H(C$_2$H$_5$)—), 25.01 ($\underline{C}$H$_2$CH$_3$), 12.00 (—$\underline{C}$H$_3$)

Chiral analysis was performed using a Chiralcel AD-H column using n-hexane/isopropanol (98/2) mobile phase, flow 1.0 mL/min; t$_R$ (R-enantiomer, major): 14.9 min; t$_R$ (S-enantiomer, minor): 16.3 min, e.e. 98%.

Example 3: (R)-3-phenylbutan-1-ol (R)-ethyl 3-phenylbutyrate (200 mg, 1.04 mmol, 1 equiv., 99.0% ee), manganese catalyst (7.5 mg, 0.001 mmol, 0.01 equiv.), potassium carbonate (14 mg, 0.10 mmol, 0.1 equivalents) and 1-methylnaphthalene (~50 μL, internal standard) was added to a microwave vial containing a stirring bead. The vial was sealed and evacuated and refilled with argon. This was repeated twice. Degassed isopropanol (2.4 mL) was added and the vial septum as pierced with 2×18G needles and placed in a stainless-steel autoclave under argon atmosphere. The vessel was pressurised with hydrogen gas (50 bar) and vented to the atmosphere. This was repeated twice. The pressure was set to 50 bar using hydrogen gas and the autoclave sealed and placed in a pre-heated oil bath (50° C.) and the stirring as set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by hexane/ethyl acetate (1/1) to give the (R)-3-phenylbutan-1-ol as a colourless oil (150 mg, 96%).

$^1$H-NMR (CDCl$_3$) δ: 7.33 (2H, m, Ph-H), 7.23 (3H, m, Ph-H), 3.58 (2H, m, C$\underline{H}_2$OH), 2.91 (1H, m, PhC$\underline{H}$(CH$_3$)), 1.88 (2H, m, —C$\underline{H}_2$—), 1.30 (2H, d, J=7.8 Hz, —C$\underline{H}_3$)

$^{13}$C-{$^1$H}-NMR (CDCl$_3$) δ: 146.82 ($\underline{C}_{Ar}$), 128.50 ($\underline{C}_{Ar}$), 126.97 ($\underline{C}_{Ar}$), 126.14 ($\underline{C}_{Ar}$), 61.23 (—$\underline{C}$H$_2$OH), 40.99 (Ph$\underline{C}$H(CH$_3$)—), 36.46 ($\underline{C}$H$_2$), 22.44 (—$\underline{C}$H$_3$)

HRMS (EI+): calculated for [C$_{10}$H$_{14}$O]: 150.1045 found: 150.1043

Chiral analysis was performed using a Chiralcel OD-H column using n-hexane/isopropanol (98/2) mobile phase, flow 1.0 mL/min; t$_R$ (S-enantiomer, minor): 21.2 min; t$_R$ (R-enantiomer, major): 25.1 min, e.e. 99%.

Example 4: (S)—N,N-dibenzyvalinol (S)-benzyl N,N-dibenzylvaline (289 mg, 0.75 mmol, 1 equiv., 99.8% ee), manganese catalyst (5.4 mg, 0.0075 mmol, 0.01 equiv.), potassium carbonate (10 mg, 0.075 mmol, 0.1 equivalents) and 1-methylnaphthalene (~50 μL, internal standard) was added to a microwave vial containing a stirring bead. The vial was sealed and evacuated and refilled with argon. This was repeated twice. Degassed isopropanol (2.5 mL) was added and the vial septum as pierced with 2×18G needles and placed in a stainless-steel autoclave under argon atmosphere. The vessel was pressurised with hydrogen gas (50 bar) and vented to the atmosphere. This was repeated twice. The pressure was set to 50 bar using hydrogen gas and the autoclave sealed and placed in a pre-heated oil bath (110° C.) and the stirring as set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by hexane/diethyl ether (4/1) to give the (S)—N,N-dibenzylvalinol as a colourless oil (160 mg, 75%).

$^1$H-NMR (CDCl$_3$) δ: 7.33 (4H, m, Ph-H), 7.27 (6H, m, Ph-H), 3.91 (2H, d, J=13.5 Hz, PhC$\underline{H}_2$N), 3.60 (2H, d, J=13.5 Hz, PhC$\underline{H}_2$N), 3.68 (1H, dd, J=11.0 Hz/3.6 Hz CH$_2$OH), 3.46 (1H, dd, J=10.7 Hz/4.7 Hz, CH$_2$OH), 2.56 (1H, m, —C$\underline{H}$—), 2.09 (1H, m, —C$\underline{H}$—), 1.17 (3H, d, J=6.6 Hz, —C$\underline{H}_3$), 0.91 (3H, d, J=6.6 Hz, —C$\underline{H}_3$)

$^{13}$C-{$^1$H}-NMR (CDCl$_3$) δ: 139.68 ($\underline{C}_{Ar}$CH$_2$N), 129.22 ($\underline{C}_{Ar}$), 128.46 ($\underline{C}_{Ar}$), 127.16 ($\underline{C}_{Ar}$), 64.66 (—$\underline{C}$H$_2$OH), 59.24 (Ph$\underline{C}$H$_2$N), 54.20 (—$\underline{C}$H—), 27.63 (—$\underline{C}$H—), 22.80 (—$\underline{C}$H$_3$), 20.14 (—$\underline{C}$H$_3$)

HRMS (ES+): calculated for [C$_{17}$H$_{24}$ON$^+$]: 284.2009 found: 284.2002

Chiral analysis was performed using a Chiralcel OD-H column using n-hexane/isopropanol (90/10) mobile phase, flow 1.0 mL/min; t$_R$ (R-enantiomer, minor): 7.5 min; t$_R$ (S-enantiomer, major): 7.9 min, e.e. 99.8%.

Example 5: (S)—N,N-dibenzylphenylaninol (S)-ethyl N,N-dibenzylphenylalanine (670 mg, 1.76 mmol, 1 equiv., 99.8% ee) and 1-methylnaphthalene (~50 µL, internal standard) was dissolved in degassed isopropanol (7.0 mL). Manganese catalyst (13.0 mg, 0.018 mmol, 0.01 equiv.) and potassium carbonate (24.8 mg, 0.10 mmol, 0.1 equiv.) was added to a glass insert containing a stirring bar and the insert put in an autoclave fitted with a vacuum/gas inlet and a charging port. The autoclave was sealed and evacuated and refilled with argon. This was repeated twice. The substrate solution was added via the charging port, and the vessel pressurised with hydrogen gas (50 bar) and vented to the atmosphere. This was repeated twice. The pressure was set to 50 bar using hydrogen gas and the autoclave sealed and placed in a pre-heated oil bath (110° C.) and the stirring as set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by hexane/diethyl ether (90/10) to give the (S)—N,N-dibenzylphenylaninol as a white solid (400 mg, 66%).

$^1$H-NMR (CDCl$_3$) δ: 7.38-7.27 (12H, m, Ph-H), 7.22 (1H, m, Ph-H), 7.14 (2H, d, J=7.7 Hz, Ph-H), 3.96 (2H, d, J=13.8 Hz, PhCH$_2$N), 3.54 (3H, m, PhCH$_2$N and —CH—), 3.37 (1H, s, —OH), 3.13 (2H, m, —CH$_2$OH), 3.05 (1H, m, —CH$_2$—), 2.47 (1H, m, —CH$_2$—)

$^{13}$C-{$^1$H}-NMR (CDCl$_3$) δ: 139.16 (C$_{Ar}$CH$_2$N), 139.08 (C$_{Ar}$CH$_2$—), 129.04 (C$_{Ar}$), 129.04 (C$_{Ar}$), 127.35 (C$_{Ar}$), 126.27 (C$_{Ar}$), 60.88 (—CH$_2$OH), 60.32 (PhCH$_2$—), 53.25 (PhCH$_2$N), 31.74 (—CH—)

Chiral analysis was performed using a Chiralcel OD-H column using n-hexane/isopropanol (90/10) mobile phase, flow 1.0 mL/min; t$_R$ (R-enantiomer, minor): 10.2 min; t$_R$ (S-enantiomer, major): 13.3 min. e.e. 99.8%.

Example 6: (S)—N,N-dibenzyallylglycinol (S)-Benzyl N,N-dibenzylallylglycine (400 mg, 1.04 mmol, 1 equiv., 98% ee), manganese catalyst (7.5 mg, 0.01 mmol, 0.01 equiv.), potassium carbonate (14 mg, 0.10 mmol, 0.1 equivalents) and 1-methylnaphthalene (~50 µL, internal standard) was added to a glass insert containing a stirring bar and the insert put in an autoclave fitted with a vacuum/gas inlet and a charging port. The autoclave was sealed and evacuated and refilled with argon. This was repeated twice. Degassed isopropanol (6.0 mL) was added via the charging port and the vessel was pressurised with hydrogen gas (50 bar) and vented to the atmosphere. This was repeated twice. The pressure was set to 50 bar using hydrogen gas and the autoclave sealed and placed in a pre-heated oil bath (50° C.) and the stirring as set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by hexane/diethyl ether (90/10) to give the (S)—N,N-dibenzylallyl glycinol as a colourless oil (212 mg, 76%).

$^1$H-NMR (CDCl$_3$) δ: 7.36-7.26 (10H, m, Ph-H), 5.77 (1H, m, —CH=CH$_2$), 5.14-5.06 (2H, m, —CH=CH$_2$), 3.88 (2H, d, J=13.9 Hz, PhCH$_2$N), 3.47 (4H, m, PhCH$_2$N and —CH$_2$OH), 3.07 (1H, s, —OH), 2.92 (1H, m, —CH(NBn$_2$)—), 2.56 (1H, m, —CH$_2$—), 2.00 (1H, m, —CH$_2$—), $^{13}$C-{$^1$H}-NMR (CDCl$_3$) δ: 139.12 (C$_{Ar}$CH$_2$N), 135.38 (C$_{Ar}$), 129.05 (C$_{Ar}$), 128.53 (C$_{Ar}$), 127.29 (C$_{Ar}$), 117.05 (C$_{Ar}$), 60.69 (—CH$_2$OH), 55.68 (—CH=CH$_2$), 53.22 (—CH=CH$_2$), 29.66 (—CH$_2$—)

Chiral analysis was performed using a Chiralcel OD-H column using n-hexane/isopropanol (90/10) mobile phase, flow 0.5 mL/min; t$_R$ (R-enantiomer, minor): 10.9 min; t$_R$ (S-enantiomer, major): 16.1 min, e.e. 98%.

Example 7: (R)-(−)-Ambradiol

Degassed ethanol (50 mL) was added to an autoclave, containing a glass insert and a magnetic stirrer bar, followed by manganese catalyst (14 mg, 0.020 mmol, 0.001 equiv.), potassium carbonate (276 mg, 2.00 mmol, 0.10 equiv.) and (R)-sclareolide (5000 mg, 20.0 mmol, 1.0 equiv.) under an argon atmosphere. The vessel was sealed and pressurised to 50 bar using hydrogen gas and vented. This was repeated twice followed by a final pressurisation to 50 bar using hydrogen gas. The vessel was placed in a pre-heated oil bath at 90° C. and left for 16 h with stirring (1000 rpm), then cooled to ambient temperature and vented. The reaction was analysed by $^1$H-NMR. The clear yellow solution was concentrated to 15 mL volume and water (75 mL) was added to precipitate the product. The product was filtered off and washed with water (30 mL) and petroleum ether (60/40, 50 mL) and dried to give (R)-sclareoldiol as a white solid (3.8 g, 75%).

$^1$H-NMR (CDCl$_3$) δ: 3.81 (1H, m, —CH$_2$OH), 3.49 (1H, m, —CH$_2$OH), 1.90 (1H, d, J=12.9 Hz, —CH—), 1.66 (8H, m, Aliphatic-H), 1.45 (5H, m, Aliphatic-H), 1.22 (3H, s, —CH$_3$), 1.16 (1H, m, Aliphatic-H), 0.98 (1H, m, Aliphatic-H), 0.95 (1H, m, Aliphatic-H), 0.91 (3H, s, —CH$_3$), 0.81 (6H, s, —CH$_3$)

$^{13}$C-{$^1$H}-NMR (CDCl$_3$) δ: 73.16 (—C(CH$_3$)OH), 64.22 (—CH$_2$OH), 59.07, 56.01, 44.32, 41.88, 39.32, 33.42, 33.29, 27.88, 24.70, 21.49, 20.49, 18.41, 15.32 (Aliphatic-C)

HRMS (EI+): calculated for [C$_{16}$H$_{30}$O$_2$—H$_2$O]: 236.2140 found: 236.2179 [α$_D^{20}$]: −17.2 (c. 1.00, CHCl$_3$)

Example 8: (2S)-2-[Bis(phenylmethyl)amino]-1H-indole-3-propan-1-ol (S)-ethyl N,N-dibenzyltryptophan (1.0 g, 2.42 mmol, 1 equiv., 99.8% ee) and 1-methylnaphthalene (~50 µL, internal standard) was dissolved in degassed isopropanol (7.0 mL). Manganese catalyst (17.5 mg, 0.024 mmol, 0.01 equiv.) and potassium carbonate (33.5 mg, 0.24 mmol, 0.1 equiv.) was added to a glass insert containing a stirring bar and the insert put in an autoclave fitted with a vacuum/gas inlet and a charging port. The autoclave was sealed and evacuated and refilled with argon. This was repeated twice. The substrate solution was added via the charging port, and the vessel pressurised with hydrogen gas (50 bar) and vented to the atmosphere. This was repeated twice. The pressure was set to 50 bar using hydrogen gas and the autoclave sealed and placed in a pre-heated oil bath (110° C.) and the stirring was set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by ethyl acetate to give the (S)—N,N-dibenzyltryptphanol as a white solid (830 mg, 92%).

$^1$H-NMR (CDCl$_3$) δ: 8.09 (1H, s, NH), 7.85-7.25 (12H, m, Ar—H), 7.22 (1H, t, J=8.2 Hz, Ar—H), 7.13 (1H, t, J=8.1 Hz, Ar—H), 6.93 (1H, s, Ar—H), 4.02 (2H, d, J=12.9 Hz, PhC$\underline{H}_2$N), 3.63 (2H, d, J=12.9 Hz, PhC$\underline{H}_2$N), 3.57 (1H, d, J=10.2 Hz, C$\underline{H}_2$OH), 3.47 (1H, dd, J=10.5 Hz/4.3 Hz, C$\underline{H}_2$OH), 3.30 (2H, m, —C$\underline{H}_2$—), 2.70 (1H, m, —C$\underline{H}$—)

$^{13}$C-{$^1$H}-NMR (CDCl$_3$) δ: 139.31 ($\underline{C}_A$,CH$_2$N), 136.29 ($\underline{C}_{Ar}$), 129.05 ($\underline{C}_{Ar}$), 128.54 ($\underline{C}_{Ar}$), 127.30 ($\underline{C}_{Ar}$), 122.13 ($\underline{C}_{Ar}$), 121.96 ($\underline{C}_{Ar}$), 119.31 ($\underline{C}_{Ar}$), 118.70 ($\underline{C}_{Ar}$), 112.93 ($\underline{C}_{Ar}$), 111.21 ($\underline{C}_{Ar}$), 61.00 (—$\underline{C}$H$_2$OH), 59.47 (Ph$\underline{C}$H$_2$N), 53.28 (—$\underline{C}$H—), 20.79 (—$\underline{C}$H$_2$—)

HRMS (ES+): calculated for [C$_{25}$H$_{27}$ON$_2^+$]: 371.2118 found: 371.2110

[α$_D^{20}$]: +44.5 (c. 1.00, CHCl$_3$)

Chiral analysis was performed using a Chiralcel AD-H column using n-hexane/isopropanol (90/10) mobile phase, flow 1.0 mL/min; t$_R$ (R-enantiomer, minor): 27.0 min; t$_R$ (S-enantiomer, major): 31.0 min, e.e. 99.8%.

Example 9: (S)-2-(4-isobutylphenyl)propan-1-ol (S)-ethyl ibuprofen (235 mg, 1.00 mmol, 1 equiv., 99.0% ee), manganese catalyst (7.3 mg, 0.001 mmol, 0.01 equiv.), potassium carbonate (14 mg, 0.10 mmol, 0.1 equivalents) and 1-methylnaphthalene (~50 μL, internal standard) was added to a microwave vial containing a stirring bead. The vial was sealed and evacuated and refilled with argon. This was repeated twice. Degassed isopropanol (2.8 mL) was added and the vial septum was pierced with 2×18G needles and placed in a stainless-steel autoclave under argon atmosphere. The vessel was pressurised with hydrogen gas (50 bar) and vented to the atmosphere. This was repeated twice. The pressure was set to 50 bar using hydrogen gas and the autoclave sealed and placed in a pre-heated oil bath (50° C.) and the stirring was set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by dichloromethane/methanol (95/5) to give the (S)-2-(4-isobutylphenyl)propan-1-ol as a colourless oil (185 mg, 96%).

$^1$H-NMR (CDCl$_3$) δ: 7.17 (2H, d, J=8.4 Hz, Ar—H), 7.13 (2H, d, J=8.4 Hz, Ar—H), 3.71 (2H, d, J=7.6 Hz, —C$\underline{H}_2$OH), 2.95 (1H, m, ArC$\underline{H}$—), 2.48 (2H, d, J=7.8 Hz, —C$\underline{H}_2$Ar), 1.88 (1H, m, —C$\underline{H}$—), 1.29 (3H, d, J=6.9 Hz, —C$\underline{H}_3$), 0.93 (6H, d, J=6.3 Hz, —(C$\underline{H}_3$)$_2$)

$^{13}$C-{$^1$H}-NMR (CDCl$_3$) δ: 140.68 ($\underline{C}_{Ar}$), 140.09 ($\underline{C}_{Ar}$), 129.48 ($\underline{C}_{Ar}$), 127.17 ($\underline{C}_{Ar}$), 68.81 (—$\underline{C}$H$_2$OH), 45.04 (—$\underline{C}$H—), 42.04 (Ar$\underline{C}$H$_2$—), 30.24 (—$\underline{C}$H—), 22.43 (—$\underline{C}$H$_3$), 17.63 (—$\underline{C}$H$_3$)

Chiral analysis was performed using a Chiralcel AD-H column using n-hexane/isopropanol (90/10) mobile phase, flow 1.0 mL/min; t$_R$ (R-enantiomer, minor): 20.0 min; t$_R$ (S-enantiomer, major): 21.2 min, e.e. 98.5%.

Example 10: (S)-2-(4-chlorophenyl)-2-methylbutan-1-ol (S)-ethyl 3-methyl-(4-chlorophenyl)-butyrate (241 mg, 1.00 mmol, 1 equiv., 97% ee), manganese catalyst (7.3 mg, 0.001 mmol, 0.01 equiv.), potassium carbonate (14 mg, 0.10 mmol, 0.1 equivalents) and 1-methylnaphthalene (~50 μL, internal standard) was added to a microwave vial containing a stirring bead. The vial was sealed and evacuated and refilled with argon. This was repeated twice. Degassed isopropanol (2.8 mL) was added and the vial septum was pierced with 2×18G needles and placed in a stainless-steel autoclave under argon atmosphere. The vessel was pressurised with hydrogen gas (50 bar) and vented to the atmosphere. This was repeated twice. The pressure was set to 50 bar using hydrogen gas and the autoclave sealed and placed in a pre-heated oil bath (50° C.) and the stirring was set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography using 100% hexane followed by dichloromethane/methanol (95/5) to give the (S)-2-(4-chlorophenyl)-2-methylbutan-1-ol was a colourless oil (181 mg, 91%).

$^1$H-NMR (CDCl$_3$) δ: 7.32 (2H, d, J=8.6 Hz, Ar—H), 7.26 (2H, d, J=8.6 Hz, Ar—H), 3.95 (1H, dd, J=10.8/4.8 Hz, —C$\underline{H}_2$OH), 3.83 (1H, dd, J=10.8/4.8 Hz, —C$\underline{H}_2$OH), 2.52 (1H, m, ArC$\underline{H}$—), 1.93 (1H, m, —C$\underline{H}$—), 1.02 (3H, d, J=6.6 Hz, —(C$\underline{H}_3$)$_2$), 0.75 (3H, d, J=6.6 Hz, —(C$\underline{H}_3$)$_2$)

$^{13}$C-{$^1$H}-NMR (CDCl$_3$) δ: 140.33 ($\underline{C}_{Ar}$—Cl), 132.37 ($\underline{C}_{Ar}$), 130.06 ($\underline{C}_{Ar}$), 128.70 ($\underline{C}_{Ar}$), 65.06 (—$\underline{C}$H$_2$OH), 55.16 (—$\underline{C}$H—), 29.99 (—$\underline{C}$H$_3$), 20.86 (—$\underline{C}$H$_3$)

Chiral analysis was performed using a Chiralcel AD-H column using n-hexane/isopropanol (99/1) mobile phase, flow 1.0 mL/min; t$_R$ (R-enantiomer, minor): 27.1 min; t$_R$ (S-enantiomer, major): 34.0 min. e.e. 96%.

Additional hydrogenations were conducted to illustrate the utility of different bases in accordance with the invention, as summarised in the data in Table 2 immediately below:

TABLE 2

Demonstration that productive hydrogenation of an ester can be realised using a variety of weaker base co-catalysts than are generally used

| Base | pKa | Solvent | Conversion | Product |
|---|---|---|---|---|
| None | N/A | Isopropanol | 0% | 0% |
| KO$^t$Bu[1] | 17 | Isopropanol | >99% | >99% |
| K$_2$CO$_3$ | 10.3 | Isopropanol | >99% | >99% |

TABLE 2-continued

Demonstration that productive hydrogenation of an ester can be realised using a variety of weaker base co-catalysts than are generally used 50 bar H$_2$
0.1 mol % Mn Cat
10 mol % base
Solvent, 90° C., 16 h

| Base | pKa | Solvent | Conversion | Product |
|---|---|---|---|---|
| K$_2$CO$_3$ | 10.3 | Ethanol | >99% | >99% |
| KHCO$_3$ | 6.4 | Isopropanol | 1.8% | 1.8% |
| K$_3$PO$_4$ | 12.3 | Isopropanol | >99% | >99% |
| KOH | 14 | Isopropanol | >99% | >99% |
| Na$_2$CO$_3$ | 10.3 | Isopropanol | 27% | 27% |

Synthesis of (R$_c$,S$_p$)—N-2-picolinyl-1-[2-bis(4-methoxy-3,5-dimethylphenyl)-phosphine]-ferrocenylethylamine (3)

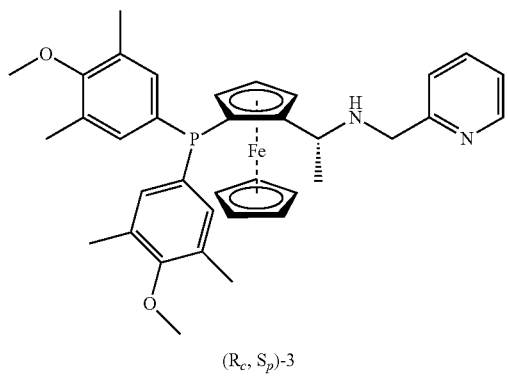

(R$_c$, S$_p$)-3

(R$_c$,S$_p$)—N,N-dimethyl-1-[2-bis(4-methoxy-3,5-dimethylphenyl)phosphine]-ferrocenylethylamine (1.0 g, 1.79 mmol, 1.0 equiv.) was added to degassed acetic anhydride (5 mL) and stirred at room temperature for 16 h. The volatiles were removed in vacuo using toluene to azaeotropically remove residual acetic anhydride. The crude material was dissolved in degassed dry methanol (10 mL) and 2-aminomethylpyridine (0.37 mL, 3.59 mmol, 2.0 equiv.) was added. The mixture was refluxed for 4 h then cooled to room temperature and volatiles removed in vacuo. The crude material was added to degassed dichloromethane (10 mL) and degassed saturated aqueous sodium bicarbonate (10 mL). The organic layer was cannulated to a Schlenk flask containing magnesium sulfate. The aqueous layer was extracted with dichloromethane (10 mL) two times, each layer cannulated to the same Schlenk flask as described above. The combined dried organic layer was filtered using a cannula fitted with a filter paper to a round bottom flask and evaporated to dryness. The crude material was purified by column chromatography using dichloromethane/methanol (9/1) to give the target compound as a yellow foam (0.84 g, 1.35 mmol, 76%).

$^1$H-NMR (CDCl$_3$) δ: 8.38 (1H, br d, J=4.8 Hz, C$_{Ar}$H), 7.40 (1H, t, J=7.8 Hz, C$_{Ar}$H), 7.22 (1H, S, C$_{Ar}$H), 7.21 (1H, s, C$_{Ar}$H), 7.02 (1H, t, J=6.7 Hz, C$_{Ar}$H), 6.92 (1H, s, C$_{Ar}$H), 6.90 (1H, S, C$_{Ar}$H), 6.59 (1H, d, J=7.8 Hz, C$_{Ar}$H), 4.54 (1H, m, Fc-H), 4.32 (1H, m, Fc-H), 4.23 (1H, m, —CH—), 4.06 (5H, s, Fc-H), 3.83 (1H, s, Fc-H), 3.77 (3H, m, —OCH$_3$), 3.62 (2H, br s, PyCH$_2$N—), 3.57 (3H, s, —OCH$_3$), 2.31 (6H, s, —CH$_3$), 2.09 (6H, s, —CH$_3$), 1.58 (3H, br s, CHCH$_3$, overlapped with water peak);

$^{31}$P{$^1$H}-NMR (CDCl$_3$) δ: −27.3 ppm;

HRMS: (ES+) calculated for [C$_{36}$H$_{42}$FeN$_2$O$_2$P]$^+$ 621.2328; found 621.2316;

Synthesis of [(R$_c$,S$_p$)—N-2-picolynyl-1-(~2-bis(4-methoxy-3,5-dimethylphenyl)-phosphino)ferrocenylethylamine]-κN$^1$-κN$^2$-κP-tricarbonyl manganese (I) bromide (4)

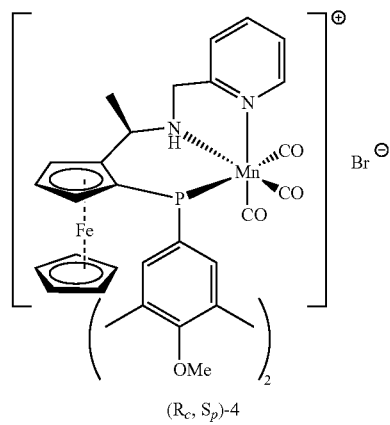

(R$_c$, S$_p$)-4

(R$_c$,S$_p$)—N-2-picolinyl-1-(2-bis(4-methoxy-3,5-dimethylphenyl)phosphine)-ferrocenylethylamine (205 mg, 0.33 mmol, 1.02 equiv.) and bromopentacarbonylmanganese (I) (89 mg, 0.32 mmol, 1.0 equiv.) were stirred in degassed cyclohexane (10 mL) at room temperature under an argon atmosphere. The mixture was refluxed for 16 h under which time an orange slurry formed. The mixture was cooled to room temperature, diluted with $^n$pentane (20 mL), filtered, washed with $^n$pentane (2×20 mL) and dried to give the title compound as a yellow solid (200 mg, 0.26 mmol, 82%). Analysis showed the presence of cyclohexane.

$^1$H-NMR (DCM-d$_2$) δ: 8.60 (1H, br d, J=4.8 Hz, C$_{Ar}$H), 7.65 (1H, S, C$_{Ar}$H), 7.62 (1H, S, C$_{Ar}$H), 7.33 (1H, t, J=6.9 Hz, C$_{Ar}$H), 6.79 (2H, m, C$_{Ar}$H), 6.29 (1H, S, C$_{Ar}$H), 6.28 (1H, S, C$_{Ar}$H), 5.58 (1H, m, —CH—), 4.87 (1H, s, NH), 4.62 (1H, s, Fc-H), 4.48 (1H, s, Fc-H), 4.35 (1H, s, Fc-H), 4.11 (1H, m, PyCH$_2$NH—), 3.85 (5H, s, Fc-H), 3.81 (3H, s, —OCH$_3$), 3.68 (1H, m, PyCH$_2$NH), 3.54 (3H, s, —OCH$_3$), 2.40 (6H, s, —CH$_3$), 1.96 (6H, s, —CH$_3$), 1.70 (3H, br d, J=7.0 Hz, CHCH$_3$), 1.44 (cyclohexane);

$^{13}$C{$^1$H}-NMR (CDCl$_3$) δ: 159.71 (C$_{Ar}$), 158.96 (C$_{Ar}$), 156.65 (C$_{Ar}$), 152.87 (C$_{Ar}$), 135.80 (C$_{Ar}$), 135.02 (C$_{Ar}$), 134.91 (d, J$_{PC}$=11.3 Hz, C$_{Ar}$), 134.20 (C$_{Ar}$), 133.82 (C$_{Ar}$), 131.26 (C$_{Ar}$), 130.93 (d, J$_{PC}$=10.2 Hz, C$_{Ar}$), 130.33 (d, J$_{PC}$=11.3 Hz, C$_{Ar}$), 129.93 (d, J$_{PC}$=10.1 Hz, C$_{Ar}$), 122.31 (C$_{Ar}$), 119.16 (C$_{Ar}$), 91.40 (d, J$_{PC}$=19.3 Hz, Fc-C$^{ipso}$—P) 73.27 (d, J$_{PC}$=28.9 Hz, C$_{Fc}$), 72.84 (C$_{Fc}$), 70.58 (C$_{Fc}$), 69.84 (C$_{Fc}$), 59.70 (OCH$_3$), 59.32 (OCH$_3$), 56.48 (Fc-CH(CH$_3$)—

N), 59.27 ($C_{Fc}$), 48.66 (PyCH$_2$), 26.93 (cyclohexane), 20.43 (Fc-CH(CH$_3$)—N), 16.14 (Ar—CH$_3$), 15.54 (Ar—CH$_3$);

$^{31}$P-{$^1$H}-NMR (DCM-d$_2$) δ: +86.8 (s);

IR (ATR): 2927.9 (w), 1924.9 (s), 1845.9 (s), 1473.6 (m), 1217.1 (w), 1111.0 (m), 1008.8 (m), 771.5 (w), 615.3 (m) cm$^-$;

HRMS: (ES+): expected [C$_{39}$H$_{41}$FeMnN$_2$O$_3$P]$^+$: 759.1478, found: 759.1462;

Hydrogenation of Ethyl p-Fluorobenzoate Using 4

Ethyl p-fluorobenzoate (3.5 g, 20.81 mmol, 1.0 equiv.) was dissolved in ethanol (30 mL) and degassed by bubbling argon gas through the solution for 1 h. [(R$_c$,S$_p$)—N-2-picolynyl-1-(~2-bis(4-methoxy-3,5-dimethylphenyl)phosphino)ferrocenylethylamine]-κN$^1$—κN$^2$-κP-tricarbonyl manganese (I) bromide (6) (17.5 mg, 0.021 mmol, 0.001 equiv.) and potassium carbonate (288 mg, 2.08 mmol, 0.10 equiv.) was charged to an autoclave. The vessel was sealed and pressurised with hydrogen gas (5 bar) and vented. This was repeated twice. The degassed ethanol solution was added via an injection port and stirring was started (1300 rpm). The vessel was pressurised to 20 bar using hydrogen gas and then vented. This was repeated twice. The vessel was pressurised to 2 bar of hydrogen gas and heated to an internal temperature of 90° C., at which time the pressure was increased to 20 bar and the reaction started. After 18 h the vessel was cooled to room temperature and vented to atmospheric pressure. The yellow solution was analysed by $^1$H-NMR to confirm full conversion. The crude mixture was concentrated to dryness and purified by column chromatography (using dichloromethane/methanol 95/5) to give p-fluorobenzyl alcohol as a colourless oil (2.36 g, 18.73 mmol, 90%).

Further Examples of Hydrogenation Using 4

General Hydrogenation Procedure

Substrate (1.0 equivalent) was added to a Schlenk flask together with 1-methylnaphthalene (0.25 equiv.) and ethanol (3.2 mL) and degassed by bubbling argon gas through the solution for at least 30 min. To a microwave vial containing a magnetic bead was added catalyst and base (0.10 equiv.). The vial was capped and put under an inert atmosphere using vacuum/argon cycles (3). The degassed substrate solution was added to the vial under argon. The vial was pierced by two 18G needles and placed in a stainless-steel autoclave under argon atmosphere. The vessel was sealed and pressurized with hydrogen gas to 50 bar. The pressure was released, and the procedure repeated twice. Finally, the vessel was pressurized with hydrogen gas (50 bar), sealed and placed in a pre-heated oil-bath at the designated reaction temperature (90° C.) for 16 h. The vessel was cooled to ambient temperature and the pressure slowly released. The vial was uncapped, and an aliquot was taken, diluted with deuterated chloroform and analysed by $^1$H-NMR to assess the conversion using 1-methylnaphthalene as internal standard. The crude products were purified by column chromatography (as detailed below).

4-Fluorobenzyl Alcohol

The product was purified by column chromatography using 100% hexane followed by dichloromethane/methanol (95/5) to give the title compound as a colourless oil. 250 mg (1.49 mmol) ethyl p-fluorobenzoate with 0.001 equiv. 4 gave 170 mg (1.35 mmol) p-fluorobenzyl alcohol (90%);

$^1$H-NMR (CDCl$_3$) δ: 7.39 (2H, m, Ar—H), 7.10 (2H, m, Hz, Ar—H), 4.70 (2H, s, Ar—CH$_2$OH);

$^{13}$C-{$^1$H}-NMR (CDCl$_3$) δ: 163.30 ($\underline{C}_{Ar}$—F), 136.59 ($\underline{C}_{Ar}$—CH$_2$OH 128.81 ($\underline{C}_{Ar}$—H), 115.50 ($\underline{C}_{Ar}$—H), 64.72 (Ar—CH$_2$OH);

$^{19}$F-{$^1$H}-NMR (CDCl$_3$): δ: −114.89;

HRMS (EI+): calculated for [C$_7$H$_7$FO]: 126.0481, found: 126.0477.

1-Hydroxymethylnaphthalene

The product was purified by column chromatography using 100% hexane followed by ethyl acetate/hexane (1/1) to give the title compound as a white solid. 300 mg (1.50 mmol) ethyl 1-naphthanoate with 0.01 equiv. 4 gave 165 mg (1.05 mmol) 1-hydroxymethylnaphthalene (70%);

$^1$H-NMR (CDCl$_3$) δ: 8.15 (1H, d, J=7.5 Hz, Ar—H), 7.91 (1H, d, J=7.9 Hz, Ar—H), 7.85 (1H, d, J=8.4 Hz, Ar—H), 7.56 (3H, m, Ar—H), 7.48 (1H, m, Ar—H), 5.17 (2H, d, J=3.9 Hz, Ar—C$\underline{H}_2$OH), 1.91 (1H, m, Ar—CH$_2$O$\underline{H}$);

$^{13}$C-{$^1$H}-DEPT NMR (CDCl$_3$) δ: 136.26 ($\underline{C}_{Ar}$—$\overline{\underline{C}H_2}$—), 133.80 ($\underline{C}_{Ar}$), 131.23 ($\underline{C}_{Ar}$), 128.69 ($\underline{C}_{Ar}$), 128.61 ($\underline{C}_{Ar}$), 126.37 ($\underline{C}_{Ar}$), 125.91 ($\underline{C}_{Ar}$), 125.91 ($\underline{C}_{Ar}$), 125.36 ($\underline{C}_{Ar}$), 123.66 ($\underline{C}_{Ar}$), 63.72 (—$\underline{C}H_2$OH);

HRMS (EI+): calculated for [C$_{11}$H$_{10}$O]: 158.0732 found 158.0729.

(R)-Sclareodiol

The crude reaction solution was concentrated to ⅓ volume and filtered to remove inorganic material. The mother liquor was diluted with water to precipitate the product as a white solid which was isolated by filtration, washed with water and hexanes and air dried. (R)-Sclareolide (300 mg, 1.20 mmol, 1.0 equiv.) with 0.001 equiv. 4 gave 228 mg sclareodiol (0.9 mmol, 75% isolated yield).

$^1$H-NMR (CDCl$_3$) δ: 3.81 (1H, m, —C$\underline{H}_2$OH), 3.49 (1H, m, —C$\underline{H}_2$OH), 1.90 (1H, d, J=12.9 Hz, —C$\underline{H}$—), 1.66 (8H, m, Aliphatic-H), 1.45 (5H, m, Aliphatic-H), 1.22 (3H, s, —C$\underline{H}_3$), 1.16 (1H, m, Aliphatic-H), 0.98 (1H, m, Aliphatic-H), 0.95 (1H, m, Aliphatic-H), 0.91 (3H, s, —C$\underline{H}_3$), 0.81 (6H, s, —C$\underline{H}_3$);

$^{13}$C-{$^1$H}-NMR (CDCl$_3$) δ: 73.16 (—$\underline{C}$(CH$_3$)OH), 64.22 (—$\underline{C}$H$_2$OH), 59.07, 56.01, 44.32, 41.88, 39.32, 33.42, 33.29, 27.88, 24.70, 21.49, 20.49, 18.41, 15.32 (Aliphatic-C);

HRMS (EI+): calculated for [C$_{16}$H$_{30}$O$_2$—H$_2$O]: 236.2140 found: 236.2179;

[α]$_D^{20}$: −17.2 (c. 1.00, CHCl$_3$).

Synthesis of (R$_c$,S$_p$)-1-(2-bis(4-methoxy-3,5-dimethylphenyl)phosphine)-ferrocenylethylamine L-tartrate salt (5)

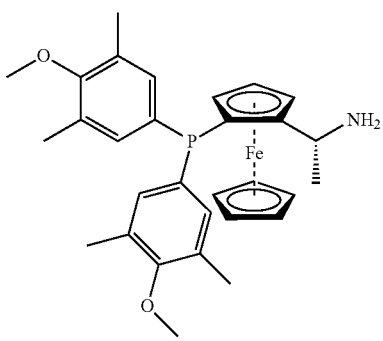

($R_c$, $S_p$)-5 (Shown without Tartrate Salt)

($R_c$,$S_p$)—N,N-dimethyl-1-(2-bis(4-methoxy-3,5-dimethylphenyl)phosphine)-ferrocenylethylamine (6.3 g, 11.3 mmol) was stirred in degassed acetic anhydride (30 mL) at room temperature or 16 h. The volatiles were removed by evaporation and the crude acetate dissolved in a degassed mixture of methanol (60 mL) and THF (60 mL). Aqueous ammonium hydroxide (30 wt %, 60 mL) was added and the mixture heated to 60° C. for 2 h, then cooled to room temperature and all the volatiles removed in vacuo. The crude mixture was treated with degassed saturated aqueous sodium bicarbonate (60 mL) and extracted with degassed dichloromethane (3×60 mL). The organic extracts were cannulated to a Schlenck flask containing magnesium sulfate under an argon atmosphere. The combined extracts were filtered using a cannula fitted with a filter paper into a flask and the solvent removed. The crude material was dissolved in degassed ethanol (60 mL) and L-tartaric acid (1.44 g, 9.6 mmol, 0.85 equiv.) added. The mixture was heated to reflux under an argon atmosphere and distilled to half-volume, cooled to room temperature and the product salt precipitated by the addition of diethyl ether (200 mL). Isolation by filtration and washing with diethyl ether gave the title compound as a yellow solid (6.0 g, 8.8 mmol, 78% yield).

$^1$H-NMR (MeOD) δ: 7.29 (1H, S, $C_{Ar}$H), 7.27 (1H, S, $C_{Ar}$H), 6.87 (1H, S, $C_{Ar}$H), 6.86 (1H, S, $C_{Ar}$H), 4.97 (7H, br s, H2O, —OH, —NH$_2$, CO$_2$H), 4.69 (1H, s, Fc-H), 4.56 (2H, br s, —CH— and Fc-H), 4.43 (2H, m, HO$_2$C(CH)$_2$CO$_2$H), 4.12 (1H, m, Fc-H), 4.05 (5H, s, Fc-H), 3.77 (3H, s, —OCH$_3$), 3.71 (3H, s, —OCH$_3$), 2.32 (6H, s, —CH$_3$), 2.20 (6H, s, —CH$_3$), 1.79 (3H, br d, J=8.1 Hz, CHCH$_3$);

$^{13}$C{$^1$H}-NMR (CDCl$_3$) δ: 158.33 (s, $C_{Ar}$), 157.40 (s, $C_{Ar}$), 135.41 (s, $C_{Ar}$), 135.23 (s, $C_{Ar}$), 134.06 (d, $J_{PC}$=5.9 Hz, $C_{Ar}$), 132.68 (s, $C_{Ar}$), 132.53 (s, $C_{Ar}$), 131.46 (d, $J_{PC}$=5.8 Hz, $C_{Ar}$), 131.02 (d, $J_{PC}$=7.3 Hz, $C_{Ar}$), 130.07 (d, $J_{PC}$=9.7 Hz, $C_{Ar}$), 91.02 (d, $J_{PC}$=26.8 Hz, Fc-$C^{ipso}$—P), 76.3 (d, $J_{PC}$=11.3 Hz, $C_{Fc}$), 72.80 (C), 72.37 (HO$_2$C(CHOH)$_2$CO2H), 70.05 ($C_{Fc}$), 69.77 ($C_{Fc}$), 69.19 ($C_{Fc}$), 58.83 (—OCH$_3$), 57.83 (—OCH$_3$), 46.30 (d, $J_{PC}$=9.7 Hz, Fc-CH(CH$_3$)—N), 19.15 (Fc-CH(CH$_3$)—N), 14.88 (Ar—CH$_3$);

$^{31}$P{$^1$H}-NMR (CDCl$_3$) δ: −28.7 (s);

IR (ATR, cm$^{-1}$): 2927.9 (m), 2358.9 (w), 2160.3 (m), 2019.5 (w), 1473.6 (m), 1273.0 (m), 1217.1 (s), 1109.1 (s), 1072.4 (s), 1010.7 (s), 817.8 (m), 678.9 (m), 607.6 (m);

HRMS: (ES+) calculated for [C$_{30}$H$_{37}$FeNO$_2$P]$^+$ 530.1906; found 530.1890;

Synthesis of 4-(dimethylamino)pyridine-2-carboxaldehyde (6)

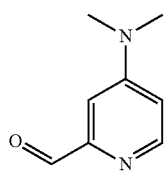

2-dimethylaminoethanol (1.7 mL, 17.0 mmol, 2.1 equiv.) was dissolved in $^n$hexane (20 mL) and cooled to −10° C. under an inert atmosphere. N-Butyl lithium (1.6 M, 20 mL, 32 mmol, 3.9 equiv.) was slowly added to the cold solution. The resulting clear colourless solution was stirred at −10° C. for 30 min then 4-dimethylaminopyridine (1.0 g, 8.2 mmol, 1.0 equiv.) was added as a solid. The yellow slurry was stirred at −10° C. for 2 h then cooled to −78° C. and dimethylformamide (1 mL, 12.9 mmol, 1.6 equiv.) in THF (15 mL) was added. 1 M aqueous hydrochloric acid (50 mL) was added after 1 h and the mixture allowed to warm to room temperature and the layers separated. The aqueous layer was found to have a pH of 1 and was extracted with diethyl ether (3×50 mL). The organic extractions were discarded. The pH was adjusted to 7 using solid sodium bicarbonate and the mixture again extracted with diethyl ether (3×50 mL). The combined organic layers were dried over magnesium sulfate, filtered and concentrated to dryness to give the title compound as a pale brown oil (0.65 g, 4.3 mmol, 53%).

$^1$H-NMR (CDCl$_3$) δ: 10.01 (1H, s, —CHO), 8.40 (1H, d, J=6.0 Hz, $C_{Ar}$H), 7.20 (1H, d, J=2.8 Hz, $C_{Ar}$H), 6.68 (1H, dd, J=6.0/2.8 Hz, $C_{Ar}$H), 6.10 (1H, d, J=2.1 Hz, $C_{Ar}$H), 3.09 (6H, s, —N(CH$_3$)$_2$);

$^{13}$C-{$^1$H}-NMR (CDCl$_3$) δ: 194.59 (—CHO), 154.70 ($C_{Ar}$), 152.95 ($C_{Ar}$), 150.05 ($C_{Ar}$), 109.87 ($C_{Ar}$), 104.37 ($C_{Ar}$), 39.24 (—N(CH$_3$)$_2$).

Synthesis of ($R_c$, $S_p$)—N-[4-(dimethylamino)pyridine-2-methyl]-1-(2-bis(4-methoxy-3, 5-dimethylphenyl)phosphine)ferrocenylethylamine L-tartrate salt (7)

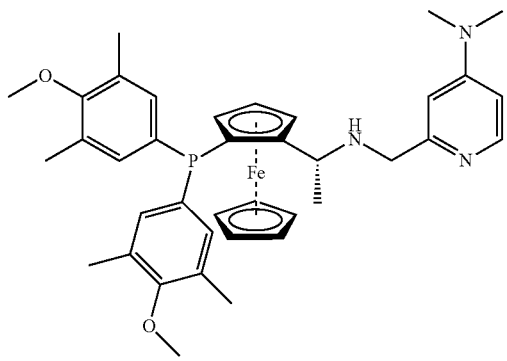

($R_c$, $S_p$)-7 (Shown without Tartrate Salt)

($R_c$, $S_p$)-1-(2-bis(4-methoxy-3,5-dimethylphenyl)phosphine)ferrocenylethylamine (2.1 g, 4.0 mmol, 1.0 equiv.) was treated with 4-(dimethylamino)pyridine-2-carboxaldehyde (0.60 g, 4.0 mmol, 1.0 equiv.) and stirred at room temperature in degassed dry methanol (20 mL) for 2 h. Sodium borohydride (303 mg, 8.0 mmol, 2.0 equiv.) was added and the resulting mixture stirred for another 2 h at room temperature under an inert atmosphere. Volatiles were removed in vacuo and the crude material added to saturated aqueous sodium bicarbonate (20 mL) and extracted with dichloromethane (3×20 mL). The extracts were cannulated to a Schlenk flask containing magnesium sulfate. The dried combined organic extracts were filtered using a cannula fitted with a filter paper and concentrated to give ($R_c$, $S_p$)—N-[4-(dimethylamino)pyridine-2-methyl]-1-(2-bis(4-methoxy-3,5-dimethylphenyl)phosphine)-ferrocenylethylamine as an orange foam (2.6 g, 3.92 mmol, 98%). 200 mg (0.30 mmol, 1.0 equiv.) was treated with 45 mg (0.30 mmol, 1.0 equiv) of L-tartaric acid in isopropanol (5 mL) as per the previous description (see synthesis of compound 3) to give the title compound as a yellow solid (147 mg, 0.18 mmol, 60%).

$^1$H-NMR (MeOD) δ: 7.81 (1H, br s, Py-H), 7.25 (1H, s, $C_{Ar}$H), 7.23 (1H, S, $C_{Ar}$H), 6.91 (1H, S, $C_{Ar}$H), 6.90 (1H, S, $C_{Ar}$H), 6.77 (1H, br s, Py-H), 6.36 (1H, br s, Py-H), 4.94 (12H, br s, H$_2$O, —OH, —NH$_2$, CO$_2$H), 4.64 (1H, s, Fc-H), 4.48 (3H, br s, HO$_2$C(C$\underline{H}$)$_2$CO$_2$H and Fc-H), 4.43 (1H, br s, —C$\underline{H}$(CH$_3$)—), 4.04 (5$\underline{H}$, s, Fc-H), 4.02 (1H, s, Fc-H), 3.76 (3$\overline{H}$, —OCH$_3$), 3.61 (3H, s, —OCH$_3$), 3.53 (2H, m, —CH$_2$Py), 3.13 (6H, s, —N(C$\underline{H}_3$)$_2$), 2.30 (6H, s, —CH$_3$), 2.09 (6H, s, —CH$_3$), 1.79 (3H, br d, J=7.5 Hz, CHC$\underline{H}_3$);

$^{13}$C{$^1$H}-NMR (MeOD) δ: 158.09 (s, $C_{Ar}$), 157.24 (s, $C_{Ar}$), 151.59 (s, $C_{Ar}$), 139.09 (s, $C_{Ar}$), 135.25 (s, $C_{Ar}$), 135.08 (s, $C_{Ar}$), 134.75 (d, $J_{PC}$=8.6 Hz, $C_{Ar}$), 133.0 (s, $C_{Ar}$), 132.84 (s, $C_{Ar}$), 131.30 (d, $J_{PC}$=6.6 Hz, $C_{Ar}$), 130.81 (d, $J_{PC}$=6.6 Hz, $C_{Ar}$), 130.49 (d, $J_{PC}$=8.6 Hz, $C_{Ar}$), 105.83 ($C_{Ar}$), 103.75 (s, $C_{Ar}$), 94.64 (d, $J_{PC}$=26.4 Hz, Fc-$C^{ipso}$—P) 76.06 (d, $J_{PC}$=8.2 Hz, Cc), 72.72 (HO$_2$C(C$\underline{H}$OH)$_2$CO$_2$H), 71.57 ($C_{Fc}$), 69.53 ($C_{Fc}$), 69.24 ($C_{Fc}$), 69.19 ($C_{Fc}$), 58.83 (—OCH$_3$), 57.83 (—OCH$_3$), 51.74 (d, $J_{PC}$=10.4 Hz, Fc-$\underline{C}$H(CH$_3$)—N), 45.79 (s, —CH$_2$Py), 38.67 (s, —N($\underline{C}$H$_3$)$_2$), 17.70 (Fc-CH($\underline{C}$H$_3$)—N), 14.78 (Ar—$\underline{C}$H$_3$);

$^{31}$P-{$^1$H}-N$\overline{M}$R (CDCl3) δ: −28.4 (s);

IR (ATR): 2922.2 (w), 2358.9 (w), 1639.5 (m), 1556.6 (m), 1473.6 (w), 1273.0 (w), 1217.1 (s), 1111.0 (s), 1006.8 (s), 817.8 (m), 609.5 (m) cm$^{-1}$;

HRMS: (ES+) calculated for [C$_{38}$H$_{47}$FeN$_3$O$_2$P]$^+$ 664.2750; found 664.2733

Synthesis of [(R$_c$,S$_p$)—N-(4-(dimethylamino)pyridine-2-methyl)-1-(~2-bis(4-methoxy-3,5-dimethylphenyl)phosphino)ferrocenylethylamine]-κN$^1$-κN$^2$-κP-tricarbonyl manganese (I) bromide (8)

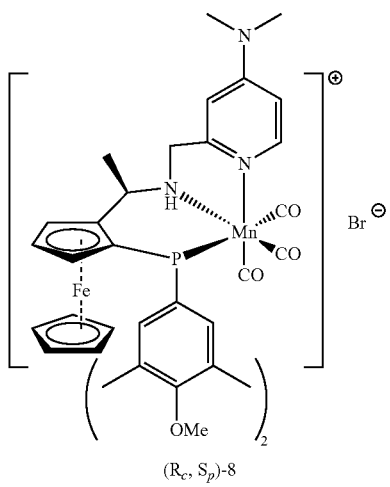

(R$_c$, S$_p$)-8

(R$_c$,S$_p$)—N-(4-dimethylaminopyridine-2-methyl)-1-(2-bis(4-methoxy-3,5-dimethyl-phenyl)phosphine)ferrocenylethylamine (2.4 g, 3.62 mmol, 1.02 equiv.) and bromopentacarbonylmanganese (I) (975 mg, 3.55 mmol, 1.0 equiv.) were stirred in degassed cyclohexane (50 mL) at room temperature under an argon atmosphere. The mixture was refluxed for 16 h under which time an orange slurry formed. The mixture was cooled to room temperature, diluted with "hexane (40 mL), filtered, and washed with "hexane (20 mL). The crude material was dissolved in dichloromethane (10 mL) and filtered. "hexane (30 mL) was added and the resulting mixture slowly evaporated until product precipitated. The product was filtered, washed with "hexane and dried to give the title compound as a yellow solid (2.87 g, 3.27 mmol, 92%). Analysis showed two species that could not be separated.

$^1$H-NMR (DCM-d$_2$) δ (major): 8.04 (1H, br d, J=7.5 Hz, $C_{Ar}$H), 7.65 (1H, s, $C_{Ar}$H), 7.63 (1H, s, $C_{Ar}$H), 6.33 (1H, $C_{Ar}$H overlap with minor), 6.01 (2H, s, $C_{Ar}$, overlap with minor), 5.58 (1H, d, J=6.9 Hz, —CH—, overlaps with minor), 4.84 (1H, s, NH), 4.60 (1H, s, Fc-H), 4.45 (1H, s, Fc-H), 4.33 (1H, s, Fc-H), 3.95 (1H, m, PyCH$_2$NH—, overlap with minor), 3.84 (5H, s, Fc-H, overlap with minor), 3.80 (3H, s, —OCH$_3$, overlap with minor), 3.58 (1H, m, PyCH$_2$NH, overlap with minor), 3.52 (3H, s, —OCH$_3$), 2.86 (6H, s, —N(CH$_3$)$_2$, overlap with minor) 2.39 (6H, s, —CH$_3$), 1.98 (6H, s, —CH$_3$, overlap with minor), 1.68 (3H, br d, J=6.9 Hz, CHC$\underline{H}_3$, overlap with minor); δ (minor): 7.69 (1H, s, $C_{Ar}$H), 7.67 (1H, s, $C_{Ar}$H), 7.37 (1H, br d, J=6.2 Hz, $C_{Ar}$H) 6.33 (1H, $C_{Ar}$H overlap with major), 6.01 (2H, s, $C_{Ar}$, overlap with major), 5.95 (1H, s, $C_{Ar}$H), 5.58 (1H, d, J=6.9 Hz, —CH—, overlap with major), 4.93 (1H, s, NH), 4.69 (1H, s, Fc-H), 4.57 (1H, s, Fc-H), 3.95 (1H, m, PyCH$_2$NH—, overlap with major), 3.84 (5H, s, Fc-H, overlap with major), 3.80 (3H, s, —OCH$_3$, overlap with major), 3.58 (4H, m, PyCH$_2$NH and —OCH$_3$, overlap with major), 2.86 (6H, s, —N(CH$_3$)$_2$, Overlap with major) 2.43 (6H, s, —CH$_3$), 1.98 (6H, s, —CH$_3$, overlap with major), 1.68 (3H, br d, J=6.9 Hz, CHC$\underline{H}_3$, overlap with major);

$^{13}$C{$^1$H}-NMR (DCM-d$_2$) δ (major): 231.84 (d, $J_{PC}$=22 Hz, CO), 230.02 (d, $J_{PC}$=23.5 Hz, CO), 158.37 ($C_{Ar}$), 153.95 ($C_{Ar}$), 151.64 ($C_{Ar}$), 150.48 ($C_{Ar}$), 140.70 (d, $J_{PC}$=34 Hz, $C_{Ar}$), 136.85 ($C_{Ar}$), 136.43 ($O_{Ar}$), 134.25 (d, $J_{PC}$=10.0 Hz, $C_{Ar}$), 130.61 (d, $J_{PC}$=8.6 Hz, $C_{Ar}$), 130.27 ($O_{Ar}$), 127.80 ($O_{Ar}$), 127.48 (d, $J_{PC}$=10.1 Hz, $C_{Ar}$), 106.90 ($C_{Ar}$), 101.93 ($C_{Ar}$), 91.87 (d, $J_{PC}$=18.6 Hz, Fc-$C^{ipso}$—P), 72.70 ($C_{Fc}$), 70.66 ($C_{Fc}$), 56.69 (Py-$\underline{C}$H$_2$—N), 48.73 (Fc-$\underline{C}$H(CH$_3$)—N), 39.22 (—N($\underline{C}$H$_3$)$_2$), 20.58 (Fc-CH($\underline{C}$H$_3$)—N); δ (minor): 159.82 ($C_{Ar}$), 154.31 ($C_{Ar}$), 150.48 ($C_{Ar}$), 134.51 (d, $J_{PC}$=10.6 Hz, $C_{Ar}$), 131.47 ($O_{Ar}$), 131.16 ($C_{Ar}$), 128.83 ($O_{Ar}$), 128.10 (d, $J_{PC}$=8.6 Hz, $C_{Ar}$), 127.68 ($O_{Ar}$), 107.84 ($O_{Ar}$), 102.96 ($C_{Ar}$), 92.51 (d, $J_{PC}$=23.1 Hz, Fc-$C^{ipso}$—P), 73.21 ($C_{Fc}$), 71.42 ($C_{Fc}$), 70.94 ($C_{Fc}$), 70.07 ($C_{Fc}$), 58.04 (Py-$\underline{C}$H$_2$—N), 49.79 (Fc-$\underline{C}$H(CH$_3$)—N), 39.37 (—N($\underline{C}$H$_3$)$_2$), 19.64 (Fc-CH($\underline{C}$H$_3$)—N);

$^{31}$P-{$^1$H}-NMR (DCM-d$_2$) δ: +89.1 (s, major), 43.6 (br s, minor);

IR (ATR): 2953.0 (w), 2918.3 (w), 2895.2 (w), 2025.3 (s), 1942.3 (m), 1909.5 (s), 1830.5 (s), 1616.4 (s), 1473.6 (m), 1276.9 (m), 1219.0 (m), 1111.0 (s), 1008.8 (s), 839.0 (s), 617.2 (s) cm$^{-1}$;

HRMS: (ESI positive): expected [C$_{41}$H$_{46}$FeMnN$_3$O$_5$P]$^+$: 802.1900, found: 802.1889;

Comparison of Catalytic Activity Between 2 and 8 in the Hydrogenation of Ethyl p-Fluorobenzoate Ethyl p-fluorobenzoate (3.5 g, 20.81 mmol, 1.0 equiv.) was dissolved in ethanol (30 mL) and degassed for 1 h using argon gas bubbling. The catalyst (0.021 mmol, 0.001 equiv.) and potassium carbonate (288 mg, 2.08 mmol, 0.10 equiv.) was charged to an autoclave fitted with an overhead stirred, internal thermometer and a gas burette. The vessel was sealed and pressurised with hydrogen gas (5 bar) and vented. This was repeated twice. The degassed ethanol solution was added via an injection port and stirring was started (1300 rpm). The vessel was pressurised to 20 bar using hydrogen gas and then vented. This was repeated twice. The vessel was pressurised to 2 bar of hydrogen gas and heated to an internal temperature of 90° C. at which time the pressure was increased to 20 bar and the reaction started. Gas uptake was monitored by reduction of the pressure in the burette. The reaction was assumed complete when no uptake of gas was observed for >2 h. The vessel was cooled to room temperature, vented and the content concentrated to dryness and analysed by $^1$H-NMR to confirm full conversion. The uptake curve was converted to conversion by dividing the gas uptake at a time-point by the total uptake and multiplying the result by 100 to get percentage conversion. From the data, substrate and product concentrations could be calculated and from those, the turnover frequency (TOF, see Table 3 below).

TABLE 3

Comparsion of the catalytic activity of 2 and 8 in the hydrogenation of ethyl p-fluorobenzoate

| Catalyst | Temperature (° C.) | Catalyst Loading (mol %) | Reaction time (h) | Conversion (%) | TOF[c] (h$^{-1}$) |
|---|---|---|---|---|---|
| 2 | 70 | 0.2 | 16 | 100 | 104 |
| 8 | 70 | 0.1 | 16 | 96 | 368 |
| 8 | 50 | 0.2 | 15.5 | 100 | 155 |

[c]The TOF is equal to the number of molecules reacting per active site per hour, recorded at 20% conversion.

Catalysts 2 and 8 successfully catalyse the hydrogenation of ethyl p-fluorobenzoate in the presence of a weak base (potassium carbonate). Catalyst 8 is effective at temperatures of 70 and 50° C., thereby allowing for some flexibility in the temperature used for hydrogenation, and potentially broadening the substrate scope to cover esters that are unstable at higher temperatures.

Hydrogenation of (R)-Sclareolide Using 8

(R)-Sclareolide (300 mg, 1.20 mmol, 1 equiv.), catalyst 8 (2.1 mg, 0.002 mmol, 0.002 equiv.), potassium carbonate (17 mg, 0.12 mmol, 0.1 equivalents) and 1-methylnaphthalene (~50 mL, internal standard) was added to a microwave vial containing a stirring bead. The vial was sealed and evacuated and refilled with argon. This was repeated twice. Degassed ethanol (2.4 mL) was added and the vial septum as pierced with 2×18G needles and placed in a stainless-steel autoclave under an argon atmosphere. The vessel was pressurised with hydrogen gas (50 bar) and vented to the atmosphere. This was repeated twice. The pressure was set to 50 bar using hydrogen gas and the autoclave was sealed and placed in a pre-heated oil bath (50° C.). The stirring was set to 1200 rpm and the reaction was left for 16 h. After the reaction, the vessel was cooled to ambient temperature and vented to the atmosphere, the reaction was analysed by $^1$H-NMR and conversion was estimated using the internal standard (1-methylnaphthalene). Water was added to precipitate the product which was filtered off and washed with hexanes to give the product as a white solid (229 mg, 75%).

$^1$H-NMR (CDCl$_3$) δ: 3.81 (1H, m, —C$\underline{H}_2$OH), 3.49 (1H, m, —C$\underline{H}_2$OH), 1.90 (1H, d, J=12.9 Hz, —C$\underline{H}$—), 1.66 (8H, m, Aliphatic-H), 1.45 (5H, m, Aliphatic-H), 1.22 (3H, s, —C$\underline{H}_3$), 1.16 (1H, m, Aliphatic-H), 0.98 (1H, m, Aliphatic-H), 0.95 (1H, m, Aliphatic-H), 0.91 (3H, s, —C$\underline{H}_3$), 0.81 (6H, s, —C$\underline{H}_3$);

$^{13}$C-{$^1$H}-NMR (CDCl$_3$) δ: 73.16 (—$\underline{C}$(CH$_3$)OH), 64.22 (—$\underline{C}$H$_2$OH), 59.07, 56.01, 44.32, 41.88, 39.32, 33.42, 33.29, 27.88, 24.70, 21.49, 20.49, 18.41, 15.32 (Aliphatic-C);

$[\alpha]_D^{20}$: −17.2 (c. 1.00, CHCl$_3$);

HRMS (EI+): calculated for [C$_{16}$H$_{30}$O$_2$—H$_2$O]: 236.2140 found: 236.2179.

The invention claimed is:

1. A method comprising hydrogenating an ester in the presence of (i) a base, wherein the conjugate acid of the base has a pKa, determined in water at 25° C., of from 6.4 to 14, (ii) hydrogen gas and (iii) a catalyst comprising a charged or neutral complex of formula (I):

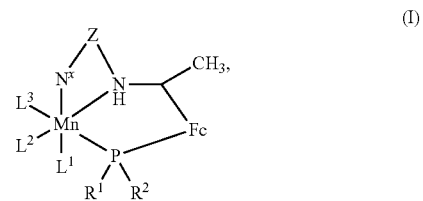

wherein:

Mn is a manganese atom or a manganese ion in oxidation state (I) to (VII);

R$^1$ and R$^2$ are independently selected from C$_{1-6}$alkyl, C$_{3-6}$cycloalkyl, phenyl, naphthyl, and furanyl, wherein the phenyl, naphthyl, and furanyl are each optionally substituted one or more times with a substituent selected from the group consisting of fluoro, chloro, C$_{1-6}$ alkyl, trifluoromethyl, and C$_{1-6}$ alkoxy;

-Fc- denotes a ferrocene (bis(η$^5$-cyclopentadienyl) iron) moiety covalently bonded via adjacent carbon atoms of one of the two cyclopentadienyl moieties;

—Z— is —(CH$_2$)—, —(CHR$^3$)— or —(CH$_2$)$_2$—, wherein R$^3$ is an C$_{1-6}$alkyl substituent or phenyl optionally substituted one or more times with C$_{1-6}$alkyl and/or halo;

—N$^x$ is selected from the group consisting of pyridyl, quinolinyl, isoquinolinyl, pyrimidinyl, oxazolyl, isooxazolyl, imidazolyl, pyrazolyl, quinoxalinyl, pyridazinyl, triazolyl, triazinyl, imidazolidinyl and oxadiazolyl, each of which is optionally substituted one or more times with one or more substituents independently selected from the group consisting of C$_{1-6}$alkyloxy, amino, halo, C$_{1-6}$alkyl, and aryl; and L$^3$ is selected from the group consisting of carbon monoxide, nitrogen monoxide, amines, ethers, thioethers, sulfoxides, nitriles, isocyanides, phosphorus-containing ligands based on either phosphorus (III) or phosphorus (V), water, halides, alkoxides, anions of carboxylic, sulfonic and phosphoric acids, amido ligands, thiolates, phosphides, cyanide, thiocyanate, isothiocyanate, and enolate ions, L$^1$ and L$^2$ are each a carbon monoxide ligand, wherein, when the complex of formula (I) is charged, the catalyst comprises one or more additional counterions to balance the charge of the complex.

2. The method of claim 1 wherein the base is selected from the group consisting of potassium carbonate, potassium phosphate, potassium hydroxide, sodium carbonate, cesium carbonate, sodium hydroxide, lithium carbonate, lithium hydroxide, calcium hydroxide, potassium bicarbonate, sodium bicarbonate, lithium bicarbonate and tertiary amines.

3. The method of claim 1 wherein the conjugate acid of the base has a pKa, determined in water at 25° C., of from 10.3 to 14.

4. The method of claim 3 wherein the base is selected from the group consisting of potassium carbonate, potassium phosphate, potassium hydroxide, sodium carbonate, cesium carbonate, sodium hydroxide, lithium carbonate, lithium hydroxide, and calcium hydroxide.

5. The method of claim 4 wherein the base is selected from the group consisting of potassium carbonate, potassium phosphate, potassium hydroxide, sodium carbonate and cesium carbonate.

6. The method of claim 1 wherein the $R^1R^2P$-Fc-CH(Me)-NH— component of the complex is 1-[bis(4-methoxy-3,5-dimethylphenyl)phosphino]-2-[1-(HN)ethyl]ferrocene; 1-[1-(HN)ethyl]-2-(diphenylphosphino)ferrocene; 1-[bis(4-methoxy-3,5-di-tert-butylphenyl)phosphino]-2-[1-(HN)ethyl]ferrocene; 1-(difuranylphosphino)-2-[1-(HN)ethyl]ferrocene; 1-[bis[3,5-bis(trifluoromethyl)phenyl]phosphino]-2-[1-(HN)ethyl]ferrocene or 1-(dicyclohexylphosphino)-2-[1-(HN)ethyl]ferrocene.

7. The method of claim 6, wherein the $R^1R^2P$-Fc-CH(Me)-NH— component of the complex is (S)-1-[bis(4-methoxy-3,5-dimethylphenyl)phosphino]-2-[(R)-1-(HN)ethyl]ferrocene, (R)-1-[bis(4-methoxy-3,5-dimethylphenyl)phosphino]-2-[(S)-1-(HN)ethyl]ferrocene or a mixture thereof; (S)-1-[(R)-1-(HN)ethyl]-2-(diphenylphosphino)ferrocene, (R)-1-[(S)-1-(HN)ethyl]-2-(diphenylphosphino)ferrocene or a mixture thereof; (S)-1-[bis(4-methoxy-3,5-di-tert-butylphenyl)phosphino]-2-[(R)-1-(HN)ethyl]ferrocene, (R)-1-[bis(4-methoxy-3,5-di-tert-butylphenyl)phosphino]-2-[(S)-1-(HN)ethyl]ferrocene or a mixture thereof; (S)-1-(difuranylphosphino)-2-[(R)-1-(HN)ethyl]ferrocene, (R)-1-(difuranylphosphino)-2-[(S)-1-(HN)ethyl]ferrocene or a mixture thereof; (S)-1-[bis[3,5-bis(trifluoromethyl)phenyl]phosphino]-2-[(R)-1-(HN)ethyl]ferrocene, (R)-1-[bis[3,5-bis(trifluoromethyl)phenyl]phosphino]-2-[(S)-1-(HN)ethyl]ferrocene or a mixture thereof; or (S)-1-(dicyclohexylphosphino)-2-[(R)-1-(HN)ethyl]ferrocene, (R)-1-(dicyclohexylphosphino)-2-[(S)-1-(HN)ethyl]ferrocene or a mixture thereof.

8. The method of claim 1, wherein —$N^x$ is a pyridyl ring optionally substituted one or more times with an amino substituent.

9. The method of claim 8, wherein —$N^x$ is 2-pyridyl or 4-dimethylaminopyridin-2-yl.

10. The method of claim 1, wherein $L^3$ constitutes a ligand selected from neutral monodentate ligands and anionic ligands.

11. The method of claim 10, wherein $L^3$ is carbon monoxide or a halide.

12. The method of claim 1, wherein the complex has a single positive charge and catalyst further comprises one halide or tetrarylborate counteranion.

13. The method of claim 1, wherein the counteranion is bromide or $[B\{3,5-(CF_3)_2C_6H_3\}_4]^-$.

14. The method of claim 1, wherein the catalyst has one of the formulae:

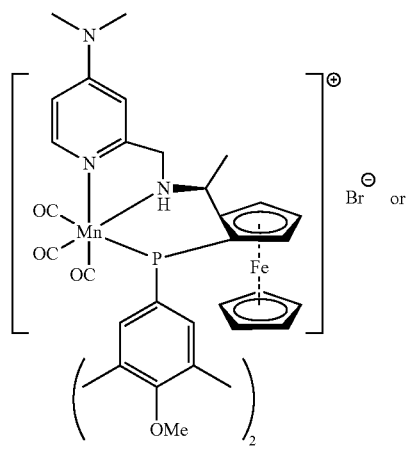

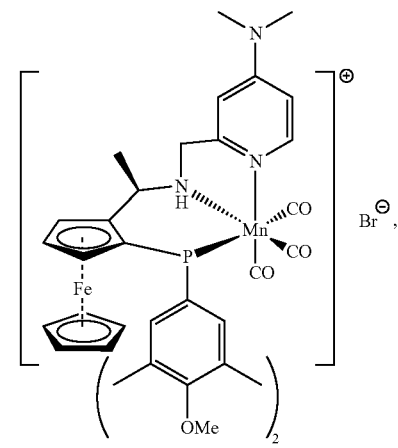

or is a mixture thereof;

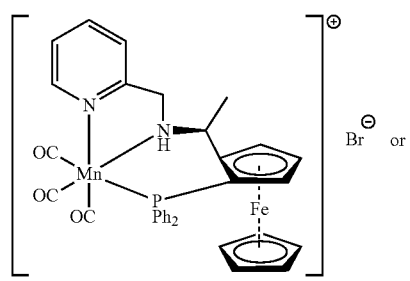

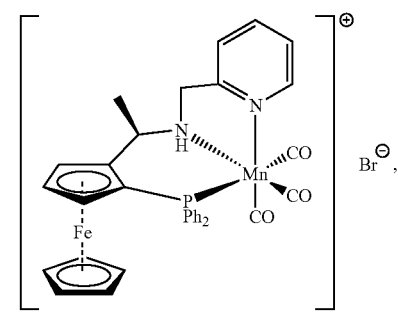

or is a mixture thereof;

49
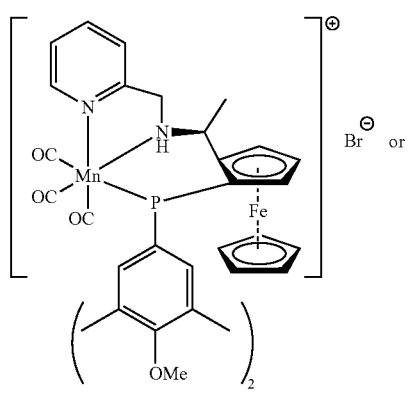
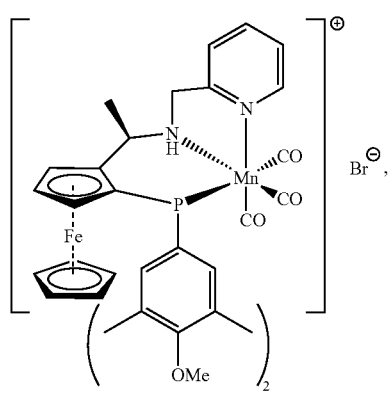
or is a mixture thereof;
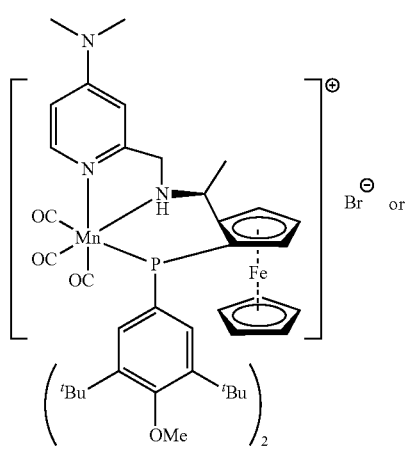
50
-continued
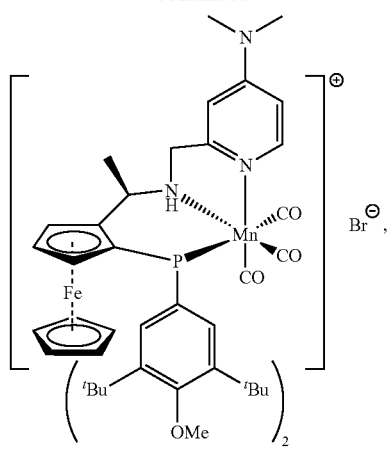
or is a mixture thereof;
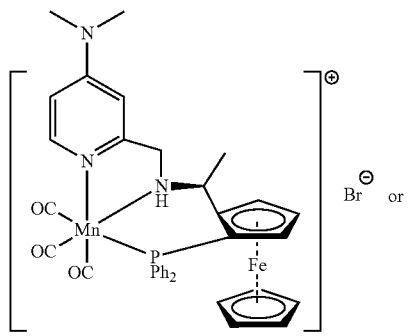
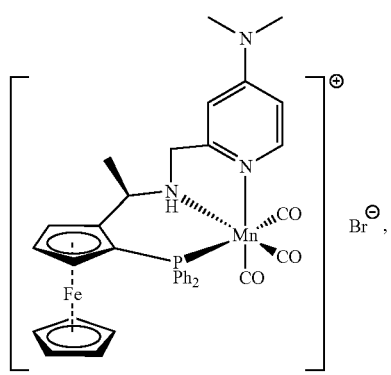
or is a mixture thereof;

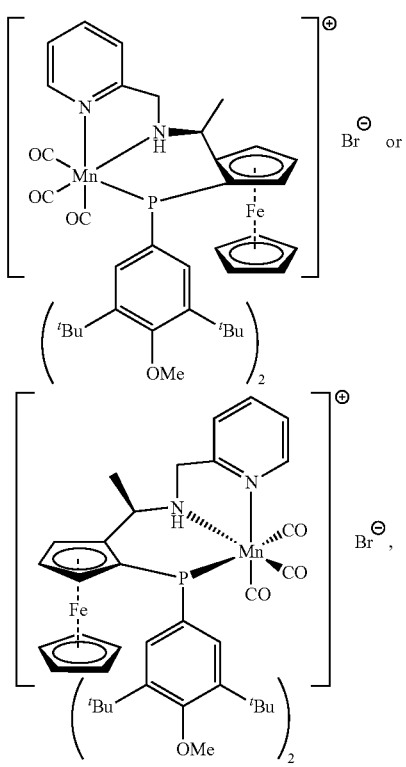

or is a mixture thereof.

15. The method of claim 1 wherein the ester is optically active.

16. The method of claim 15 wherein the ester comprises a stereogenic centre adjacent to the carbonyl group of the ester.

17. The method of claim 15 wherein the ester is sclareolide, having the formula

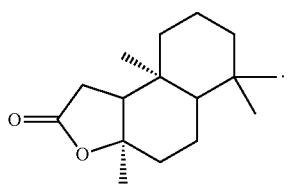 [SMILES: CC1(C)CCC[C@@]2(C)C1CC[C@@]1(C)OC(=O)CC21]

18. The method of claim 15 in which the enantiomeric excess of the optically active ester is maintained or diminished no more than 10% by the hydrogenation.

19. A method of making ambroxide comprising hydrogenating sclareolide by a method as defined in claim 17 and thereafter cyclising the resultant diol (ambradiol) whereby to provide ambroxide.

20. The method of claim 10, wherein $L^3$ is carbon monoxide or bromide.

* * * * *